(12) United States Patent
Todd et al.

(10) Patent No.: US 12,163,948 B2
(45) Date of Patent: Dec. 10, 2024

(54) APPARATUSES AND METHODS INVOLVING PROTEIN EXPLORATION THROUGH PROTEOLYSIS AND NANOPORE TRANSLOCATION

(71) Applicant: SRI International, Menlo Park, CA (US)

(72) Inventors: Kathryn G. Todd, Menlo Park, CA (US); Matthew D. Puster, San Francisco, CA (US); Keith Laderoute, Menlo Park, CA (US); Kevin Luebke, Staunton, VA (US); David Huber, Menlo Park, CA (US); Maneesh Yadav, Menlo Park, CA (US)

(73) Assignee: SRI International, Menlo Park, CA (US)

( * ) Notice: Subject to any disclaimer, the term of this patent is extended or adjusted under 35 U.S.C. 154(b) by 761 days.

(21) Appl. No.: 17/416,243

(22) PCT Filed: Dec. 21, 2018

(86) PCT No.: PCT/US2018/067149
§ 371 (c)(1),
(2) Date: Jun. 18, 2021

(87) PCT Pub. No.: WO2020/131103
PCT Pub. Date: Jun. 25, 2020

(65) Prior Publication Data
US 2022/0074920 A1  Mar. 10, 2022

(51) Int. Cl.
*G01N 27/327* (2006.01)
*G01N 27/26* (2006.01)
*G01N 33/487* (2006.01)

(52) U.S. Cl.
CPC ....... *G01N 33/48721* (2013.01); *G01N 27/26* (2013.01)

(58) Field of Classification Search
CPC .... G01N 33/48721; G01N 27/26; C07K 1/24; C07K 1/26
See application file for complete search history.

(56) References Cited

U.S. PATENT DOCUMENTS

| 6,793,753 B2 * | 9/2004 | Unger ............... B01L 3/502707 |
| | | 137/15.18 |
| 2003/0207326 A1 | 11/2003 | Su et al. |

(Continued)

FOREIGN PATENT DOCUMENTS

| WO | WO 0079257 A * | 12/2000 | ............. G01N 27/26 |
| WO | WO 2013116509 A1 * | 8/2013 | ............... C12Q 1/68 |

(Continued)

OTHER PUBLICATIONS

Kukwikila et al., "Electrically sensing protease activity with nanopores," J. Phys.: Condens. Matter 22(2010) 454103 (6pp) (Year: 2010).*

(Continued)

*Primary Examiner* — Alexander S Noguerola
(74) *Attorney, Agent, or Firm* — Dicke, Billig & Czaja, PLLC

(57) ABSTRACT

Embodiments in accordance with the present disclosure are directed to methods and apparatuses used for evaluating a protein in a sample using proteolysis and translocation. An example method includes isolating a single protein from a sample in a chamber having at least a first well and a second well separated from the first well by a membrane with a nanopore, the nanopore providing fluidic communication between the first and second wells. The single protein is cleaved into a plurality of peptide fragments via exposure to a protease in the first well, and translocated through the nanopore by applying an electric potential to the nanopore in the chamber after cleavage of the single protein by the protease. The method further includes detecting events indicative of the translocations of the plurality of peptide fragments through the nanopore and to the second well.

20 Claims, 24 Drawing Sheets

(56) References Cited

U.S. PATENT DOCUMENTS

| | | | |
|---|---|---|---|
| 2006/0105461 A1* | 5/2006 | Tom-Moy | B82Y 15/00 |
| | | | 422/63 |
| 2010/0322825 A1 | 12/2010 | Yamakawa et al. | |
| 2013/0309776 A1 | 11/2013 | Drndic et al. | |
| 2015/0087526 A1 | 3/2015 | Hesselberth | |
| 2016/0274082 A1* | 9/2016 | Yuan | C12Q 1/6869 |

FOREIGN PATENT DOCUMENTS

| | | | | |
|---|---|---|---|---|
| WO | WO 2015042200 A1 * | 3/2015 | | G01N 33/68 |
| WO | WO 2017208631 A1 * | 12/2017 | | G01N 27/00 |

OTHER PUBLICATIONS

EPO machine-generated English language translation of Yanagawa et al. WO 2017208631 A1, patented Dec. 7, 2017. (Year: 2017).*

G. Sampath, "A digital approach to protein identification and quantity estimation using tandem nanopores, peptidases, and database search," bioRxiv preprint doi: https://doi.org/10.1101/024158; this version posted Sep. 8, 2015 ( (Year: 2015).*

Wang et al. Nanopore Sensing of Botulinum Toxin Type B by Discriminating an Enzymatically Cleaved Peptide from a Synaptic Protein Synaptobrevin 2 Derivative. ACS applied materials & interfaces. Dec. 29, 2014, vol. 7, No. 1, pp. 184-192.

International Search Report for related PCT Application No. PCT/US2018/067149, mailed May 3, 2019.

* cited by examiner

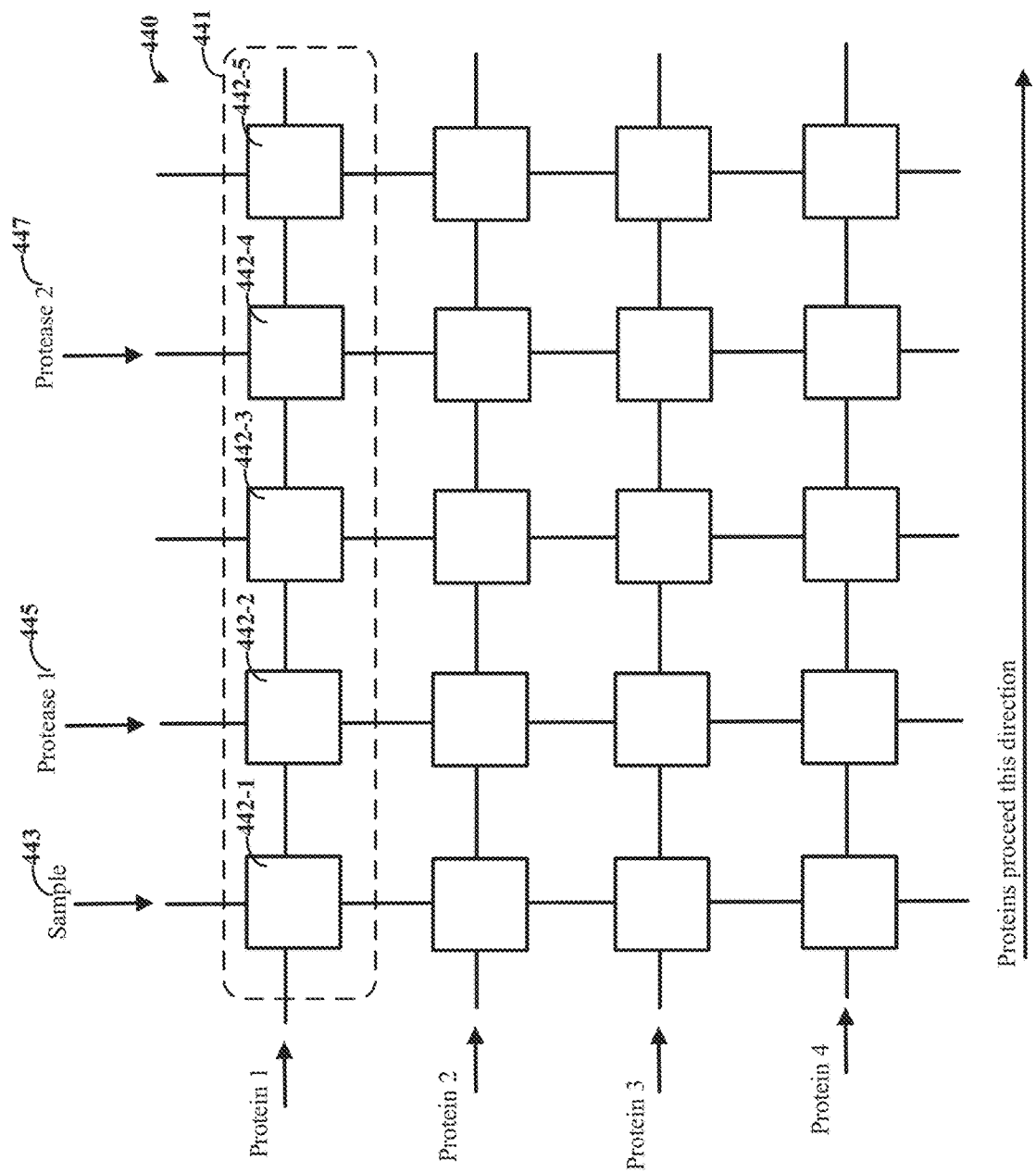

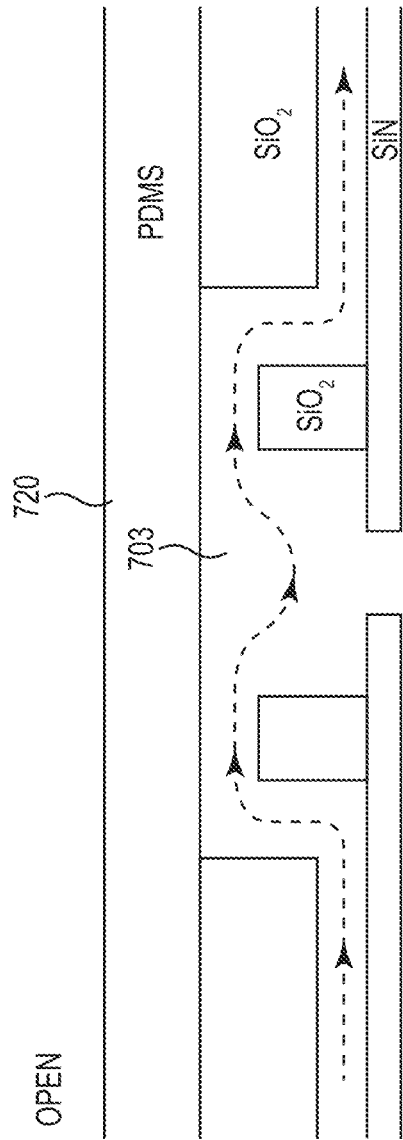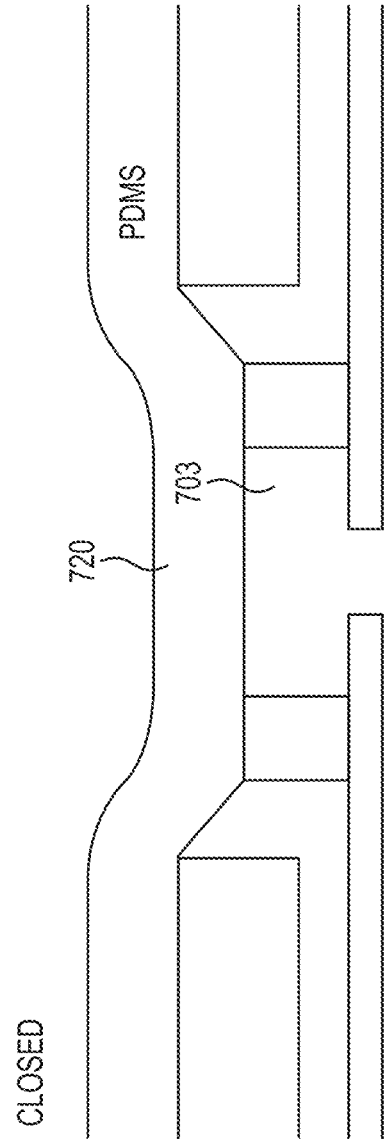
FIG. 7D
FIG. 7E

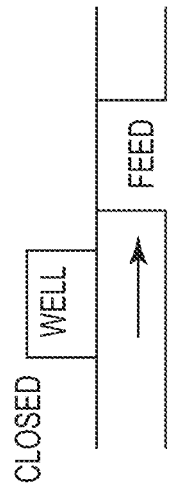
FIG. 8A
FIG. 8B
FIG. 9A
FIG. 9B

APPARATUSES AND METHODS INVOLVING PROTEIN EXPLORATION THROUGH PROTEOLYSIS AND NANOPORE TRANSLOCATION

INCORPORATION BY REFERENCE

This Utility Patent Application claims priority under 35 U.S.C. § 371 to International Application Serial No. PCT/US2018/067149, filed Dec. 21, 2018; which is incorporated herein by reference in its entirety.

OVERVIEW

Proteomic tools can be used to identify proteins for a variety of applications, including forensics, bioterrorism, and personalized medicine. Protein-based forensics can provide a variety of information for personal identification, and can complement deoxyribonucleic acid (DNA)-based evidence. A person's proteome—the set of proteins expressed, modified or imported—contains information that is not available in the genome because it is influenced by the person's (or other organism's) history and environment. For example, identical twins carry the same DNA, but can have different antibody and protein content in their blood serum. This molecular variation, which can also include indications of infection, and environmental exposure, can be used to identify a person of interest when there is insufficient DNA and can link people to locations. Protein identification can also be used to enable personalized therapeutics, decrease cost and time of biomarker discover for diagnostics (e.g., such as by 10-100 fold), and for identifying emerging bioterrorism threats from infectious agents, such as prions, engineered pathogens, and other toxins. Identification of such threats can involve protein biomarker detection in the early stages of infection, even pre-symptomatic, without the usual target-specific development of buffers and reagents. As another specific example, protein identification can be used to enable new diagnostics and treatments for warfighters that have been injured and/or exposed to infectious agents.

SUMMARY OF THE INVENTION

The present invention is directed to overcoming the above-mentioned challenges and others related to exploration of one or more proteins in a sample through proteolysis and nanopore translocation.

Various aspects of the present disclosure are directed to apparatuses and methods thereof that can be used for exploration of proteins in a sample using one or more proteolysis steps followed by translocations to count peptide fragments and to iteratively narrow down an identity of one or more of the proteins in the sample.

In various specific embodiments, a method includes isolating a single protein from a sample in a chamber having at least a first well and a second well separated from the first well by a membrane with a nanopore. As further described herein, a single protein includes or refers to a single type of protein (e.g., where there are many copies of that type or class of protein and the copies are isolated in either a single or multiple chambers but not necessarily at the single molecule level), or a single unique protein at the single molecule level. The nanopore provides fluidic communication between the at least first and second wells. The method further includes cleaving the single protein into a plurality of peptide fragments via exposure to a protease in the first well and translocating the plurality of peptide fragments through the nanopore by applying an electric potential to the chamber. The electric potential can induce an electric field, which imparts an electrophoretic force on charged peptide fragments. In some specific aspects, one or more additional forces, such as a pressure-induced force on the fluid flowing through the nanopore, can influence the peptide fragment motion. Events are detected, responsive to the electric potential, that are indicative of the translocations of the plurality of peptide fragments cut from the single protein through the nanopore and to the second well.

In various embodiments, the electric potential imparts an electrophoretic force which is generated by applying the electric potential across the nanopore. The detected events can include changes in ionic current through the nanopore. The method can further include determining an estimated number of target cleavage sites within the single protein based on the detected events, which can be indicative of the number of peptide fragments/target cleavage sites. As may be appreciated, the protease can cleave proteins by splitting peptide bonds linking at the target cleavage site (e.g., an amino acid pair). For example, the method can further include determining the estimated number of the particular target cleavage sites based on cleavage rules specific to each protease including identification of the protease that splits peptide bonds at the particular target cleavage site in the single protein and/or peptide fragments, as well as efficiency and specificity of the protease (e.g., non-primary cleavage sites and non-specific cleavage sites). Additionally, the method can include correlating the number of translocations with a percentage of the target cleavage sites, based on cleavage errors, to narrow down the identity of the single protein by iteratively introducing additional proteases.

In various-related and more specific embodiments, isolating the single protein from the sample includes flowing a solution through the chamber between the first well, the second well, and a third well, and while flowing the solution, creating a voltage differential between the first, second, and third wells. As may be appreciated and used herein, the second well and third well can include or be referred to as secondary wells. A change in ionic current is detected through one of the nanopores, which is indicative of the single protein translocating from the first well to one of the second well and third well. In response to the detection of a specific number of molecules (e.g., a specific number of proteins translocating in one or more chambers), the voltage differential can be removed. The method can further include closing fluidic access to the chamber from a remainder of the sample to isolate the single protein, which may include denatured protein(s). In various specific aspects, the detection of a specific number of molecules can be used to compensate for an error and/or to increase a confidence value.

In a number of embodiments, the above-described method can further include multiple proteolysis steps, and/or repeating of other steps, such as repeating the translocation of the peptide fragments through the nanopore and detecting the events in response thereto. As a specific example, the method can include sequentially exposing the single protein to each of a plurality of different proteases and determining numbers of peptide fragments derived from the exposure to each of the plurality of different proteases. The single protein type can be identified, with a confidence value, based on estimated numbers of target cleavage sites in the single protein determined using the detected events and a bioinformatics model. As further described herein, the bioinformatics model includes identification of a plurality of potential proteins with identified target cleavage sites, cleavage rules that each of the plurality of different proteases are subject to (e.g., protease efficiencies, non-primary cleavage sites, and non-specific cleavage sites), and non-idealities including identification of fragments that do not generate a change in ionic current (e.g., too small or charged).

In accordance with various embodiments, as described above, the chamber can include more than two wells. For example, the chamber can include the second well and a third well. The second well is separated from the first well by the membrane with a nanopore and the third well is separated from the first well by another membrane with another nanopore. The second and third wells are in fluidic communication with the first well by the respective nanopores. In such embodiments, the method further includes, after cleaving the single protein: applying a first polarity voltage to the second well and applying a second polarity voltage to the third well; detecting changes in ionic current through the nanopores, which is indicative of translocation of one of the plurality of peptide fragments cleaved from the single protein to the second and/or third wells; and determining the number of positively and negatively charged peptide fragments within the single protein (as cleaved) based on the number of detected changes in the ionic current through each respective nanopore. The net charge of the single protein can be identified based on the number of events detected through each of the nanopores, although embodiments are not so limited.

Various embodiments can include detecting clogging of the nanopore(s). The clogging can be detected based on a change in ionic current through the nanopore for greater than a threshold period time. The nanopore can be unclogged by applying a reverse bias to the nanopore.

In a number of specific embodiments, the above-described method can be used to evaluate a plurality of proteins in the sample. For example, a plurality of single proteins can be isolated from the sample in a plurality of chambers, wherein each of the plurality of chambers have at least a first well and a second well separated from the first well by a membrane with a nanopore. In such embodiments, the method further includes detecting events after cleaving each of the plurality of single proteins in each respective chamber via exposure to the protease and driving translocation.

In some specific embodiments, the nanopore can be formed in the membrane by applying a bias to the membrane. The nanopore is of a size (e.g., 1 nanometer (nm) to 50 nm in diameter with chamber dimensions of less than 500×500×500 microns) to allow translocation of the single protein (e.g., a first type of protein), without allowing simultaneous passing of a second protein (e.g., second type of protein) or such that simultaneous passing of the second single protein occurs at below a threshold frequency.

Various specific embodiments are directed to an apparatus that includes a substrate having flow channels and a plurality of chambers. The flow channels flow a sample containing a plurality of proteins there through and the plurality of chambers are in fluidic communication with the flow channels. Each of the plurality of chambers include at least a first well and two secondary wells separated from the first well by membranes having a nanopore that provides fluidic communication between the at least first well and two secondary wells. The apparatus further includes fluidic access circuitry and electrical circuitry. The fluidic access circuitry selectively provides fluidic access to the plurality of chambers and selectively provides different proteases to respective chambers to cleave the single proteins into a plurality of peptide fragments. For example, the fluidic access circuitry includes a dielectric layer that moves between an open-fluid-access state that allows fluidic access to the plurality of chambers and a closed-fluid-access state that blocks fluidic access to the plurality of chambers. Alternatively, and/or in addition, the fluidic access circuitry can include ports and/or valves. In some specific aspects, the proteases can be attached (e.g., anchored) to beads to mitigate translocation and/or denaturing. For example, the proteases are attached to beads for ease of separation, flowing of the proteases, and can be separated from the single proteins using a magnet (e.g., magnetic beads). In other embodiments, the proteases can be attached to chamber walls.

The electrical circuitry drives translocation of the single proteins and the respective plurality of peptide fragments across the nanopores and outputs electrical signals indicative of the translocations. For example, the electrical circuitry can generate or apply a voltage differential between the first well and each of the two secondary wells of each of the chambers and measures the electrical signals indicative of ionic current flowing through the respective nanopores. As previously described, a change in the ionic current is indicative of the translocations. In a number of specific embodiments, the electrical circuitry includes sets of electrodes respectively coupled to the first well and the two secondary wells of each chamber and the output electrical signals are determined from measures of each of the set of electrodes on each side of the respective membranes. The sets of electrodes apply a bias across the plurality of nanopores. As may be appreciated, an amplifier can be at each of the electrodes.

In accordance with a number of embodiments, the sample provided to the apparatus is pre-processed through a module and/or the module forms part of the apparatus. The module includes hardware and/or is configured and arranged to perform a variety of actions. For example, the module can include protease inhibitors that prevent premature proteolysis, and/or a filter that removes sample components larger in diameter than a denatured protein. In addition, alternatively, and/or in various combinations, the module can be configured to perform immunodepletion of common proteins (such as albumin) and/or fractionation by protein characteristics (e.g., protein size or some other characteristic).

In accordance with a number of embodiments, at least a portion of the above-described methods can be provided by non-transitory computer-readable storage medium. For example, the computer-readable storage medium has stored thereon program instructions executable by processing circuitry to perform at least a portion of the above-described methods. In specific embodiments, a bioinformatics model can be stored on the non-transitory computer-readable storage medium, and, similarly to a look-up table, can be used to match data to signatures for each protein.

In various embodiments, the apparatus can further include or be in communication with additional processing circuitry, which may include executable computer readable medium having instructions to cause the processing circuitry to perform various steps. For example, the processing circuitry receives the output electrical signals indicative of the translocations and in response: detects translocation of single proteins of the plurality of proteins that are in at least a portion of the plurality of chambers and communicates the detection to the fluidic access circuitry for isolating the single proteins; adjusts translocation voltages based on one or more of the number, the duration, and timing of the translocation events; detects events indicative of the translocation of the peptide fragments cuts from the single proteins through the respective nanopores responsive to exposure of the single proteins to at least one of the plurality of proteases and the electric potential; and determines the number of peptide fragments generated from the single proteins as cleaved by exposure to the protease(s) based on the number of detected events. The processing circuitry can further identify the single proteins with a confidence value based on the detected events that are responsive to sequential exposure to each of the plurality of different proteases and based on a bioinformatics model. Optionally, the processing circuitry can process signals indicative of the detected events into a measure of translocation counts that are stored on-chip, and interrogated and reset periodically by the processing circuitry (e.g., external circuitry), although embodiments are not so limited and the translation counts may not be stored on-chip. The plurality of different proteases can include at least two different proteases and in some embodiments two to six different proteases. The processing circuitry can combine information identified from detected events on multiple chambers across a single chip to produce concentration information for proteins present in the original non-homogenous sample.

Embodiments in accordance with the present disclosure include all combinations of the recited particular embodiments. Further embodiments and the full scope of applicability of the invention will become apparent from the detailed description provided hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

BRIEF DESCRIPTION OF THE DRAWINGS

Various example embodiments may be more completely understood in consideration of the following detailed description in connection with the accompanying drawings, in which:

FIG. 4A-4B illustrate an example of multiple chambers of an apparatus, in accordance with various embodiments;

FIGS. 7A-7E illustrate various example apparatuses, in accordance with various embodiments;

FIGS. 8A-8B illustrate an example of closing fluidic access to chambers, in accordance with various embodiments;

FIGS. 9A-9B illustrate an example of closing fluidic access to chambers, in accordance with various embodiments;

Figure 1:
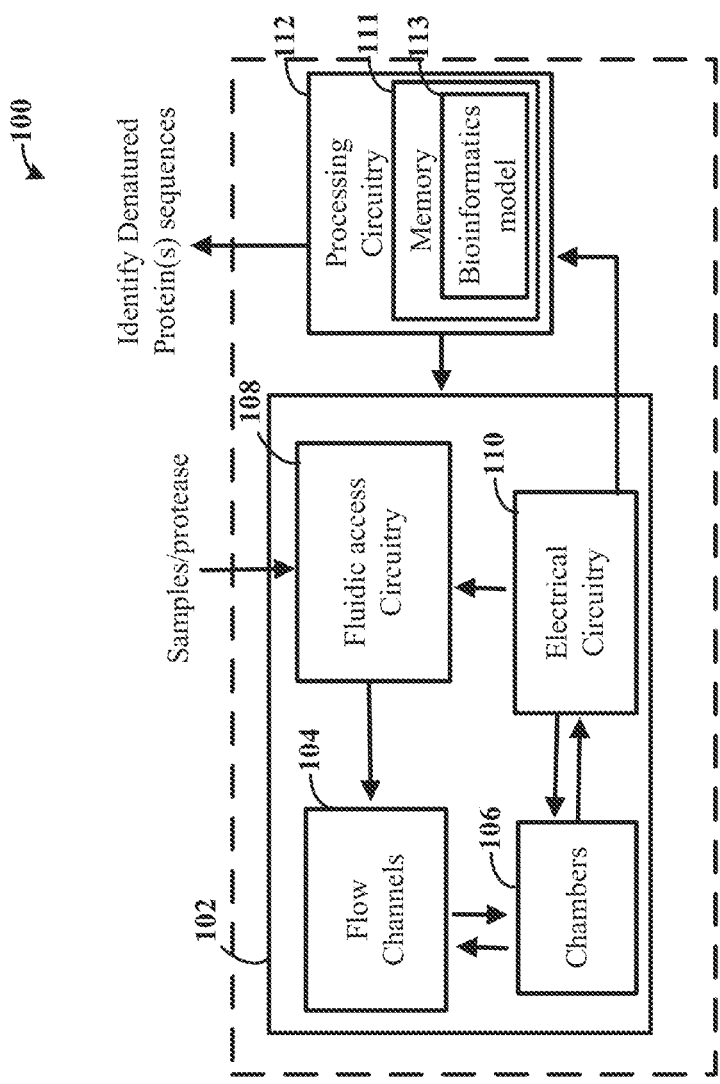
FIG. 1 illustrates an example of an apparatus, in accordance with various embodiments.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to variety of apparatuses and methods involving exploration of one or more proteins in a sample through proteolysis and nanopore translocation. In certain implementations, the apparatus includes a plurality of chambers having at least a first well and two secondary wells which are separated from the first well by membranes having a nanopore therein. A single protein can be captured by a respective chamber and cleaved via one or more proteases. Respective peptide fragments cleaved from the protein are translocated through the nanopore(s), which are detected and used to count the number of target cleaved sites associated with a respective protease. In some specific implementations, the above-described apparatus and/or method includes estimating numbers of target cleavage sites that the particular protease cuts between based on the number of peptide fragments and using the estimation to narrow down the identity of the single protein by iteratively introducing additional proteases. While the present invention is not necessarily limited to such applications, various aspects of the invention may be appreciated through a discussion of various examples using this context.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element.

Various embodiments in accordance with the present disclosure are directed to a technique of identifying one or more proteins in a sample via an apparatus and/or method involving proteolysis and nanopore translocation. Example embodiments involve proteome exploration through proteolysis and nanopore translocation and that results in proteomic measurements that are ubiquitous, sensitive, and as low-cost as genomic measurements. In various specific embodiments, the apparatus can be used to inventory a threshold number or all of the proteins in a cell or fluid sample and that can allow for drug development, rapid identification of pathogens or diagnostic markers in environmental or biological sample, among other advantages, such as those described above. Such apparatuses can be portable and applied universally (e.g., incorporates no target protein-specific reagents or labels) for a variety of different proteins in samples that may have minuet concentrations. In specific embodiments, the apparatus can identify approximately 95-97% of the human proteome, and can be a portable size of less than one cubic foot, although embodiments are not so limited. In many instances, proteins involved in regulatory function can be in low abundance, can be used to predict outcomes for diagnostic and/or or other purposes and more precisely than relatively higher-abundance proteins.

Embodiments in accordance with the present disclosure involve protein inventory through nanopore translocation and proteolysis that is used to identify proteins in a sample and can be used to identify and count proteins in the human proteome with single molecule precision. The proteolysis process can include localizing individual proteins in microscale chambers separated by solid-state nanopores, which can be approximately 1-50 (or 1-6) nm in diameter, such that the proteins travel through the nanopore one at a time under electrophoretic and/or pressure-induced force. For example, a voltage differential can be created in the chambers and by reversing the polarity of this force, the proteins can be forced to travel through the nanopore in either direction. The single proteins are trapped in chambers spread across a substrate, and in specific embodiments, such that each chamber contains no more than one single type (e.g., class) of denatured protein. At least one protease is introduced into each chamber to cleave the proteins into peptide fragments, where the number of peptide fragments generated can be determined by the abundance of the protease target sequence and the kinetics reactions. The peptide fragments are counted by translocating the fragments through the nanopore and detecting the translocation events via changes in ionic current through the nanopore. This process can be repeated for a plurality of proteases until a threshold number of the proteins that are trapped in the chambers can be identified based on a bioinformatics model that incorporates theoretical proteolysis results along with experimentally obtained results and sources of error. The iterative proteolysis and translocation of resulting fragments can be used to iteratively narrow down the identity or sequence of the single proteins.

The chambers can be filled with a buffer solution that contains free ions producing a (small) measurable current as they transverse through the nanopore. When a single protein or a peptide fragment traverses through the nanopore, it blocks a portion of the current. While the time required for a protein to pass through the pore can be indicative of its length, this quantity can be variable due to different sample solutions and surface interacts that impact the translocation speed. Nevertheless, the translocation itself can be detected from the current depression and which, in accordance with various embodiments, can be used to identify the protein and based on a counting detection modality, which can be less sensitive to noise and variation than protein identification via translocation time and/or changes in ionic current. As described above, the translocation can occur by applying an electric field, generating an electrophoretic-induced force. Deoxyribonucleic acid (DNA) molecules translocate due to the charged backbone of DNA in the presence of the voltage differential in a chamber. Proteins, in contrast, are made up of amino acid subunits that have varying isoelectric points and varying polarity. A variety of human proteins can have charges and polarity in a matrix of solution conditions, including pH, salt concentration, detergent, chaotropic denaturants, and reducing agents to allow for translocations via electrophoretic force. In some embodiments, in addition to the electrophoretic force, additional forces, such as a pressure-induced force on the fluid flowing through the nanopore can influence the fragment motion.

A variety of proteases exist that cleave proteins at specific target cleavage sites (e.g., between two amino acid pairs). Knowledge of the target cleavage sites of proteases can be used to exploit the peptide counting capability of a nanopore to obtain sufficient sequence information to unambiguously identify a protein. There are more than thirty known proteases and other agents that cleave proteins at specific target cleavage sites. Counting the number of peptide fragments produced in response to exposure of an unidentified protein to a particular protease can give sequence information. This sequence information can be used to rule out sequence homology within a large subset of proteomes. For example, a bioinformatics model can include sequence information for a proteome, such as the human proteome of around 10,000-20,000 (or more) proteins. Responsive to exposure of the unidentified protein to the particular protease, a number of the proteins in the proteome can be ruled out, such as those proteins that have too many or too few of a particular target cleavage site associated with particular protease to be the unidentified protein. The ruled out proteins may have a number of the particular target cleavage site that statistically rules out the protein. This process can be repeated, in various embodiments, to give additional information that narrows the set of possible proteins to which the unidentified protein may be. Although embodiments are not so limited, and in some specific embodiments, may include only one protease step. For example, in a specific application, ruling out a particular protein, such as when screening for a specific bioterrorism threat, may be sufficient.

The bioinformatics model is used to identify unknown proteins in a sample and includes sequence information for a plurality of known proteins. For example, the bioinformatics model includes identification of a plurality of potential proteins with identified target cleavage sites, cleavage rules that each of the plurality of different proteases are subject to (e.g., protease efficiencies, non-primary cleavage sites, and non-specific cleavage sites), and/or non-idealities including identification of peptide fragments that do not generate a change in ionic current (e.g., too small or charged). The bioinformatics model can be used to translate peptide fragment counts, including empirically-derived error estimates based on the non-idealities, with each protease iteration into a list of possible proteins from the plurality of known proteins, such as known proteins from a UnitProt database of the human proteome. With each iteration of serial peptide fragmentation, the list of possible proteins decreases and, in some embodiments, converges to a single unique type of protein (e.g., a class of protein). Protein identification can occur in parallel across a threshold number of the chambers, which can give information about the concentration of a single type of protein or a plurality of single types of proteins in the original sample.

In specific embodiments, a method for protein exploration includes isolating a single protein from a sample in a chamber having at least a first well and second well separated from the first well by a membrane with a nanopore. The nanopore can provide fluidic communication between the first and second wells. The method further includes cleaving the single protein into a plurality of peptide fragments via exposure to a protease in the first well. The plurality of peptide fragments is translocated through the nanopore by applying an electric potential across the nanopore in the chamber, such as generating an electrophoretic force, after cleavage of the single protein by the protease. The method further includes detecting events indicative of translocations of the plurality of peptide fragments cut from the single protein through the nanopore and from the first well to the second well.

The electric field (e.g., generated by a gradient in electrical potential, as found across the nanopore), in specific embodiments, imparts an electrophoretic force on charged molecules. The chambers can be filled with a buffer solution that contains free ions producing a (small) measurable current as they transverse through the nanopore. The detected events can include changes in ionic current through the nanopore, which occur due to a peptide fragment blocking the current. The method can further include determining an estimated number of target cleavage sites within the single protein based on the number of detected events. The protease can cleave proteins by splitting peptide bonds at target cleavage sites in the protein and/or respective peptide fragments. The peptide fragments refer to fragments generated by digestion of the protein via a protease. For example, the protease can cut between two amino acids and the shorter peptides fragments are counted. The method can further include correlating the number of translocations with a percentage of the target cleavage site to narrow down the identity of the single denatured protein. As a specific example, the single protein is sequentially exposed to each of a plurality of a different proteases and the number of peptide fragments derived from the exposure to each of the plurality of different proteases is determined. Further, the method can include repeating the translocation of the peptide fragments through the nanopore after exposure to a particular protease and detecting the events in response thereto by reversing the bias across the nanopore (e.g., repeat translocation process to increase accuracy of count).

In a number of embodiments, the estimated number of the particular target cleavage site(s) can be based on cleavage rules specific to each protease. The cleavage rules include or refer to identification of target cleavage sites of the protease (e.g., split peptide bonds at the target cleavage sites) and non-idealities (e.g., fragments too small, protease efficiencies, secondary cleavage sites) of the protease. More specifically, the cleavage rules can include identification of the protease that split peptide bonds at the target cleavage sites in the protein or peptide fragment and efficiency and specificity of the protease (e.g., protease efficiencies, non-primary cleavage sites and non-specific cleavage sites). As may be appreciated by one of ordinary skill, there can be multiple levels of rules regarding digestion of proteins by proteases. These rules are specific for given proteases, and while correct in the majority of cases, can be violated. Such rules are statistically meaningful rules that incorporate more specific efficiencies and errors. As a specific example of such rules, and not intending to be limiting:

Arg-C: cleaves at arginine (Arg) on the N-terminal side, the neighboring amino acid on the C-terminal side can have a moderate effect on the cleavage efficiency;

Asp-N: cleaves at aspartic acid (Asp) on the C-terminal side; and

Lys-C: cleaves at lysine (Lys) on the N-terminal side.

As may be appreciated, and as a non-limiting specific example, for analysis of trypsin, trypsin can cleave at Arg and Lys in position P1. Trypsin may cleave at higher rates for Arg, as compared to Lys at position P1, such as in the presence of high pH. When Proline (Pro) is in position P1', it may (at least sometimes) block cleavage action of trypsin. Pro may not block cleavage action of trypsin when Lys is in position P1 and tryptophan (Trp) is in position P2. Blocking of cleavage exerted by Pro in position P1' can be minor when Arg is in position P1 and methionine (Met) is in position P2 at the same time. In some instances, it may be that the block exhibited by Pro can be prevented or mitigated by glutamic acid (Glu) in P2. When Lys is in position P1, a variety of situations can block the cleavage action of trypsin. Such situations include Asp in position P2 and Asp in position P1' or cysteine (Cys) in position P2 and Asp in position P1' or Cys in position P2 and histidine (His) in position P1' or Cys in position P2 and tyrosine (Tyr) in position P1'. In further instances, trypsin cleavage action can be blocked when Arg is in P1 and either Arg in position P2 and His in position P1' or Cys in position P2 and Lys in position P1' or Arg in position P2 and Arg in position P1'. The Arg/Lys specificity can be provided with pure alpha- and beta trypsins. Trypsin that is prepared with traces of pseudotrypsin can cleave at the following amino acids in P1: phenylalanine (Phe) (except with Glu or Pro in P1'), Tyr (except with Pro and Arg in P1') and Trp (except with isoleucine (Ile), Lys, Pro, Valine (Val) and Trp in P1'), Met (with alanine (Ala), His, Met, glutamine (Gln), serine (Ser), Val and Trp in P1') and Cys (with Phe, glycine (Gly), Ile, leucine (Leu), Val and Trp in P1'). Although embodiments are not so limited, and the above is provided for illustrative purposes only, such as to illustrate examples of cleavage rules as may be appreciated by one of ordinary skill in the art and as known in the art.

In some specific embodiments, various software programs can be used to automatically predict the cleavage rules. The single protein type can be identified, with a confidence value, based on estimated numbers of target cleavage sites in the single protein determined using the detected events and the bioinformatics model. For example, the bioinformatics model can include a likelihood of cleavage based on all permutations of amino acids before and after the target cleavage sites. The likelihood of cleavage (e.g., cutting), given the neighboring amino acids, is built into the bioinformatics model.

The method can further include evaluation of a plurality of proteins in a sample at a time. For example, the method includes isolating a plurality of single proteins from the sample in a plurality of chambers. Each of the plurality of chambers have at least a first well and a second well separated from the first well by a membrane with a nanopore and a third well separated from the first well by another membrane with another nanopore. The events are detected after cleaving each of the plurality of single proteins in each respective chamber via exposure to the protease. Isolating the single protein from the sample includes flowing a solution through the chamber, and while flowing the solution, creating a voltage differential between the first well and the second well, and between the first well and the third well (e.g., applying a voltage (positive or negative)) such that the single protein is attracted to one of the second well and third well, depending on the charge of the single protein. As previous described, the second and third wells, also herein referred to as secondary wells, are on an opposite side of the membranes as the solution is flown. The method further includes detecting a change in ionic current through one of the nanopores, which is indicative of the single protein translocating to the second well or the third well, and in response to the detected change and optionally to detect a specific number of molecules translocating (e.g., to compensate for error and increase a confidence level), removing the voltage differential, thereby clamping the nanopore in the second well or the third well. The method can further include closing fluidic access to the chamber from a remainder of the sample to isolate the single protein. For example, the fluidic access can be closed to a plurality of chambers in response to a detected change in the ionic current through at least a subset of the plurality of nanopores, which indicates the subset of associated chambers respectively have a single protein therein.

After cleaving the single protein, the method includes creating a different voltage differential between the first well and second well as compared to a voltage differential between the first well and third well. For example, a first polarity (e.g., positive or ground) voltage can be applied to the second well and a second polarity (e.g., negative or ground) voltage can be applied to the third well. The method further includes detecting changes in ionic current through the nanopores, which is indicative of translocation of one of the plurality of peptide fragments as cleaved from the single protein to the second and/or third wells, and determining the number of positively and negatively charged peptide fragments based on the number of detected changes in the ionic current through each respective nanopore. In some embodiments, a sign of net charge of the single protein can be determined based on the number of events through each of the nanopores.

As a specific example, responsive to isolating the single protein in the second well, the method includes closing fluidic access to the chamber from a remainder of the sample and flowing the single protein from the second well to the first well containing the protease for incubation. A first polarity voltage is applied to the second well and a second polarity voltage is applied to a third well, wherein the first well is in fluidic communication with the second well via a first nanopore and fluidic communication with the third well via a second nanopore. The method further includes detecting the events indicative of translocation of one of the plurality of peptide fragments cleaved from the single protein through at least one of the first nanopore and the second nanopore.

In various specific embodiments, the nanopore may become clogged such as by the single protein or peptide fragment(s). The clogging of the nanopore(s) can be detected, responsive to the change in ionic current through the nanopore for greater than a threshold period of time. The nanopore can be unclogged by applying a reverse bias to the nanopore. For example, unclogging can be performed by reversing the voltage differential between the first well and second well and/or the first well and the third well.

Other specific embodiments can include methods of forming the apparatus. For example, the nanopore can be formed in the membrane by applying a bias to the membrane, although embodiments are not so limited. The nanopore may be of a size that allows translocation of single proteins. In specific embodiments, the nanopore is sized to allow passing of denatured (e.g., unfolded) single proteins and does not allow translocations of folded proteins. As specific examples, the nanopores may be 1-50 nm in diameter with the chambers having width, height, and depth dimensions of 100 nm-500 microns (µm) (e.g., 500 nm depth×20 µm width×20 µm height) to allow translocation of the single protein without allowing for simultaneous passing of a second protein or such that the likelihood of the second protein passing is below a threshold.

A specific example of forming the apparatus can include forming a plurality of chambers, each chamber having at least a first well and two secondary wells separated by respective dielectric membranes, and optionally, providing pre-thinned or otherwise weakened areas in the dielectric membranes. The method further includes forming flow channels that provide fluidic communication between the plurality of chambers. An electric potential can be applied across each of the dielectric membranes, thereby, breaking down a portion of the dielectric membrane and forming a nanopore in each of the plurality of dielectric membranes. Applying the electric potential across each of the dielectric membranes can include placing the first well at ground and applying a voltage to the two secondary wells to cause a voltage differential there between and across the dielectric membranes. The method can further include providing a feedback signal to determine a size of the nanopore and removing the voltage applied in response thereto. As may be appreciated by one of ordinary skill, embodiments are not limited to the above-described nanopore formation methods and/or methods of forming the apparatus. Example methods can include forming nanopores using transmission electron microscopy (TEM), focused ion beam (FIB), electro-chemical etching, among other techniques.

For example, nanopores can be formed in the transmission electron microscope (TEM) by focusing the electron beam to a point on the thin membrane. Upon high intensity electron exposure, a nanopore will form. The size of the nanopore can be defined by controlling the electron spot size and formation time. A similar procedure can be used in the focused ion beam (FIB) and He-ion microscope, except that instead of electrons, the nanopore is formed by interactions with ions. Track etched nanopores can be formed by exposing the membrane (typically membranes made of polycarbonate or polyester) to high energy charged particles (for example, in a nuclear reactor) and chemically etching the regions damaged by exposure.

The above-described methods can be implemented by and/or include an apparatus having flow channels, a plurality of chambers in fluidic communication with the flow channels, fluidic access circuitry, and electrical circuitry. The flow channels are used to flow a sample containing a plurality of proteins there through (and optionally, flow the proteases to the chambers). Each of the plurality of chambers includes at least a first well and two secondary wells separated from the first well by membranes having nanopores that provides fluidic communication between the at least first well and secondary wells. The secondary wells are separated from the first well by a membrane with respective nanopores. The fluidic access circuitry is used to selectively provide fluidic access to the plurality of chambers and selectively provide different proteases to respective chambers to cleave the proteins into a plurality of peptide fragments. For example, the fluidic access circuitry can include a dielectric layer that responds to a variable voltage applied thereto via the electrical circuitry by moving and/or transitioning between an open-fluid-access state that provides fluidic access to the plurality of chambers and a closed-fluid-access state that blocks fluidic access to the plurality of chambers and/or that are driven by pressure.

The electrical circuitry drives translocation of the single proteins (e.g., a plurality of different types or classes of proteins) and the respective plurality of peptide fragments across the nanopores and outputs electrical signals indicative of the translocations. The electrical circuitry provides a voltage differential between the first well and each of the two secondary wells of each of the chambers and measures the electrical signals indicative of ionic current flowing through the respective nanopores. The electrical circuitry can include sets of electrodes respectively coupled to the first well and the two secondary wells of each chamber and the output electrical signals are determined from measures of each of the set of electrodes on each side of the respective membranes. The sets of electrodes can apply a bias, e.g., voltage differential, across the plurality of nanopores, and each electrode can be associated with a power supply to apply the voltage and an amplifier to amplify and read the current.

In various specific embodiments, the apparatus further includes processing circuitry that responds to the output electrical signals indicative of the translocations. The processing circuitry can be on-chip and/or off-chip and/or otherwise separate from the other circuitry. The processing circuitry can detect translocations of single proteins of the plurality of proteins that are in at least a portion of the plurality of chambers and communicate the detection to the fluidic access circuitry for isolating the single proteins, adjust translocation voltages based on one or more of the number, duration, and timing of translocation events (e.g., turn off translocation voltage after a single translocation, reverse voltage to unclog pore after a long-duration event, or reverse the translocation polarity after a pre-determined time has passed after the last translocation event), detect events indicative of the translocation of the peptide fragments through the respective nanopores responsive to exposure of the single proteins to at least one of the plurality of proteases and the electric potential, and/or determine the number of peptide fragments based on the number of detected events. Optionally, the processing circuitry processes signals indicated of the detected events into a measure of translocation counts that are stored on-chip, and interrogated and reset periodically by the processing circuitry (e.g., external circuitry).

The processing circuitry can include or have access to the bioinformatics model. For example, the processing circuitry can identify the single proteins with a confidence value based on the detected events that are responsive to sequential exposure to each of the plurality of different proteases and based on the bioinformatics model. For example, the processing circuitry can combine information identified from detected events on multiple chambers across a single chip to produce concentration information for proteins present in the original non-homogenous sample.

In various embodiments, the bioinformatics model can be updated using feedback and by applying the above-described method(s) to a known solution. For example, the known solution can be flowed through the flow channels and the plurality of chambers, the solution containing known purified and proteins. Single proteins in at least a portion of the plurality of chambers are isolated and cleaved into a plurality of peptide fragments by exposure to at least one protease. The plurality of peptide fragments are translocated through the nanopores by applying an electric potential across the nanopores. Events are detected that are indicative of the translocations of the plurality of peptide fragments cuts from the proteins through the nanopores and to the secondary wells. The detected events are used as feedback to the bioinformatics model by identifying the isolated single proteins and comparing the detected events to the bioinformatics model. For example, the feedback can be used to identify new non-idealities and/or update the non-idealities which may be associated with particular proteases and/or peptide fragments of particular sizes. Various non-idealities may be specific to the type of apparatus used and/or the specific reaction conditions used.

Turning now to the figures, FIG. 1 illustrates an example of an apparatus, in accordance with various embodiments. The apparatus 100 can be used to explore, e.g., identify and/or assess, one or more proteins in a sample. For example, an unidentified protein can be identified, multiple proteins can be identified, and concentrations of the one or more proteins in the sample can be estimated. In specific embodiments, the apparatus 100 is used to identify and quantify the composition of single proteins in a sample, with no prior knowledge of what proteins are contained within the sample. In various embodiments, the apparatus 100 can be used to determine whether or not a particular protein is located in the sample, such as for virus or bioagent screening.

The apparatus 100 can include or be a microfluidic system 102. The microfluidic system 102 can include a microfluidic chip formed by a substrate having flow channels 104 and a plurality of chambers 106 and portable electronic circuitry (e.g., analysis circuitry). The microfluidic chip, which can be disposable, can be inserted into the portable electronic circuitry and used to evaluate proteins within a sample, thereby forming the microfluidic system 102.

The flow channels 104 are used to flow a sample containing a plurality of proteins thereto, and also optionally, flowing proteases. The sample and/or proteases can be introduced to the flow channels 104 via fluidic access circuitry 108, as further described herein. The plurality of chambers 106 are in fluidic communication with the flow channels 104. Each of the plurality of chambers 106 can include at least a first well and a second well separated from the first well by a membrane having a nanopore, as further illustrated by FIGS. 2A-2C. The nanopore provides fluidic communication between the at least first well and second well. In some specific embodiments, as illustrated further by FIGS. 4A-4B each of the chambers includes a plurality of wells arranged in a first direction (laterally), each of the plurality of wells being separated by a membrane having a nanopore. Each chamber can have a width, height, and length dimensions in the range of 10 nm-500 μm and the nanopores can be a diameter of between 1-50 nm. The membrane between the wells, and in which the nanopore is formed, can have a thickness of around 15 nm, however embodiments described herein are not so limited. As further described herein, the nanopore is used to measure the number and, optionally, the length of peptide fragments cleaved by a protease and/or a series of proteases. The nanopore can be of a diameter that is sufficient to translocate one single protein, and to a diameter that is sufficient to simultaneously translocate two single proteins, such as 1-50 nm. As previously described, the protein can be a single unique protein or a type of protein, and in some embodiments, the protein is denatured.

The fluidic access circuitry 108 selectively provides fluidic access to the plurality of chambers 106 and can selectively provide different proteases to respective chambers to cleave the proteins into a plurality of peptide fragments. The fluidic access circuitry 108, in some embodiments, includes a dielectric layer that can transition between an open-fluidic-access state and a closed-fluidic-access state that respectively allows and/or blocks fluidic access to the plurality of chambers 106. The dielectric layer can change states responsive to a variable voltage applied thereto by the electrical circuitry 110. In other embodiments and/or in addition, the fluidic access circuitry 108 can include input ports and/or valves which are selectively opened and closed.

The electrical circuitry 110 drives the translocation of the proteins and the respective plurality of peptide fragments across the nanopores. For example, the electrical circuitry 110 applies a voltage differential between the at least first and second wells of each of the plurality of chambers 106, which is used to isolate or trap single (types of) proteins in respective chambers and to selectively drive translocation of the proteins and peptide fragments through the nanopores.

The electrical circuitry 110 can output electrical signals indicative of the translocations. For example, the electrical circuitry 110 measures the electrical signals that are indicative of ionic current flowing through the nanopore and outputs the same. As previously described, the chambers 106 are filled with a buffer solution that contains free ions producing a (small) measurable current as they transverse through the nanopore. When a protein or a peptide fragment traverses through the nanopore, it blocks a portion of the current. A change in the ionic current, such as an ionic current depression, is indicative of one or more translocations. In some specific embodiments, the electrical circuitry 110 includes sets of electrodes respectively coupled to the at least first and second wells of each of the plurality of chambers 106, which are used to output electrical signals from measures of each the sets of electrodes. The sets of electrodes can apply a bias across the plurality of nanopores.

The electrical circuitry 110 can include portions that are on-chip (e.g., on the microfluidic chip) and portions that are off-chip and that form part of the portable circuitry. For example, the plurality of electrodes can be on-chip and configured to connect with additional circuitry of the portable circuitry. A voltage source and other processing circuitry used to obtain and output electrical signals can be off-chip, although embodiments are not so limited.

For example, the apparatus 100 can further include processing circuitry 112 having a memory circuit 111. The processing circuitry 112 can be part of the portable circuitry or can be separate therefrom and in communication with the electrical circuitry 110 to receive the output electrical signals. The processing circuitry 112 receives the output electrical signals which can be indicative of translocations and can use the output electrical signals to detect translocations of single proteins in at least a portion of the plurality of chambers 106. The processing circuitry 112 communicates the detection to the fluidic access circuitry 108 for isolating the single proteins. In various embodiments, the processing circuitry 112, in response to detecting a translocation of a respective single protein, communicates with the electrical circuitry 110 to cause the electrical circuitry 110 to remove the voltage differential from the chamber. Removing the voltage differential can prevent or mitigate an additional protein from translocating and being trapped in the same chamber. In response to a threshold number of chambers having isolated single proteins, the fluidic access is blocked from the plurality of chambers 106 via the fluidic access circuitry 108.

In some specific embodiments, the processing circuitry 112 can be used to detect that one or more chambers 106 has more than one single protein therein. The detection may be in response to two (or more) changes in ionic current, which may occur prior to the electrical circuitry 110 removing the voltage differential. In response the detection, the electrical circuitry 110 may drive translocation of both proteins through the nanopore for removal of the proteins. In some embodiments, the particular chamber can have a voltage differential reapplied to recapture one of the single proteins or a different single protein (e.g., a different type of protein) or can be effectively deactivated (e.g., no voltage differential and no protein captured). Although embodiments as described herein are not so limited, for example, the voltage differential can be removed in response to detection of a specific number of molecules translocating into one or more chambers. The specific number can be used to compensate for an error and/or to increase an accuracy.

The processing circuitry 112 can further be used to detect events indicative of the translocation of the peptide fragments cleaved from the single proteins (or from peptide fragments) through the respective nanopores responsive to exposure of the proteins to at least one of the plurality of proteases based on the output electrical signals. Optionally, the processing circuitry 112 adjusts translocation voltages based on one or more of the number of, duration of, and timing of translocation events (e.g. turn off translocation voltage after a single translocation, reverse voltage to unclog pore after a long-duration event, or reverse the translocation polarity after a pre-determined time has passed after the last translocation event). For example, the processing circuitry 112 can determine the number of peptide fragments cut from the single types of proteins based on the number of detected events. Optionally, the processed signals indicative of the detected events and of a measure of translocation counts are stored on-chip, and interrogated and reset periodically by the processing circuitry 112 (e.g., external circuitry). In specific embodiments, the protein types can be identified with a confidence value based on the detected events that are responsive to sequential exposure to each of the plurality of different proteases and based on a bioinformatics model. The memory circuit 111 can, for example, store the bioinformatics model 113. In various embodiments, the processing circuitry 112 can combine information identified from detected events on multiple chambers across a single chip to produce concentration information for proteins present in the original non-homogenous sample.

As previously described, the bioinformatics model 113 is used to identify unknown proteins in a sample and includes target cleavage sites (e.g., amino acid pairs that are cleaved by different proteins) for a plurality of known proteins. The bioinformatics model 113 can include an algorithm that combines known information and information generated by each of the chambers responsive to the proteolysis and translocation to determine a likely identity of a single protein trapped in a respective chamber of the plurality. The known information can include identification of a plurality of potential proteins with identified target cleavage sites, cleavage rules that each of the plurality of different proteases are subject to (e.g., protease efficiencies, non-primary cleavage sites, and non-specific cleavage sites), and non-idealities including identification of peptide fragments that do not generate a change in ionic current (e.g., too small or charged). The bioinformatics model can additionally combine identified protein counts from the plurality of chambers to generate a concentration estimate for one or more proteins detected in the sample.

The bioinformatics model 113 can be based on a database which provides a list of potential proteins. The potential proteins in the list are iteratively narrowed down after each proteolysis step, and based on the cleavage rules and non-idealities. The cleavage rules and non-idealities can be generated based on literature and further updated based on feedback from exploration with the apparatus, as further described herein. The bioinformatics model 113 can output an identification of a protein with a particular confidence value and/or identification of the presence (or not) of a particular protein with a particular confidence value.

As a specific example, and further illustrated herein, after each proteolysis and measurement cycle, the bioinformatics model 113 can be used to assign probabilities that the protein under measurement corresponds to any protein sequence or type derived from a database of possible proteins based on number of fragments detected, their sign of net charges, and system error rates. The bioinformatics model 113 can also be used to eliminate sequences of proteins from consideration if they do not meet a pre-determined likelihood threshold. As this process is repeated after each proteolysis and measurement cycle, the number of possible proteins is iteratively reduced. After the final proteolysis and measurement cycle, the highest probability protein is selected as the identified protein in that chamber, which can be referred to as the bioinformatics model's "call" for the identified protein in that chamber. By tallying the number of calls of identical proteins and comparing to the original sample volume, the bioinformatics model 113 can be used to determine an estimated concentration for a plurality of and/or each protein detected.

The bioinformatics model 113 can be revised based on feedback. For example, the non-idealities can be revised based on feedback from the apparatus 100. In some specific embodiments, the bioinformatics model 113 is revised overtime, such as using information communicated due to use of a plurality of similar-type apparatuses in different environmental conditions and/or updated knowledge based on known proteins and/or proteases. The cleavage rules used can be based on actual protease efficiencies measured in an example apparatus 100 using a proteolysis process. Additionally, the non-idealities can be updated based on the measurements, and which are made using a sample containing known proteins and concentrations.

In some instances, a plurality of proteins in a sample can be identified using a threshold plurality of proteases, such as at least two, at least four, and/or at least six different proteases. The proteases can function in high temperatures, high salt concentrations, and with detergent. For example, the proteases can be exposed to a buffer that has a high salt and high denaturing solution. Example proteases include trypsin, AspN, ArgC, Chymotrypsin, LysC, GluC among other proteases. The salt concentrations increase the magnitude of the measured signal as the magnitude of the measured signal is proportional to the concentration of salt in the solution.

As a specific example, a sample is pre-processed to purify the proteins and inserted into the microfluidic chip via an input port. In some specific embodiment, the apparatus 100 includes a module to perform pre-processing and/or the module can be external to the apparatus. The module can include protease inhibitors that prevent or mitigate premature proteolysis, and/or a filter used to remove sample components larger in diameter than a denatured protein. Alternatively and/or in addition, the module can perform immunodepletion of common proteins (such as albumin) and/or fractionation by protein characteristics (e.g., protein size or some other characteristic).

The fluidic access circuitry 108 allows fluidic access to the flow channels 104 and flows the sample including the proteins over the chambers 106 (e.g., the top chambers). The chambers 106 includes a buffer solution that may have an ionic detergent to render the proteins charged, although embodiments are not so limited and the proteins may already be charged. The charge can allow for the proteins to be driven to translocate through the nanopore. An electric potential is applied across the nanopore(s) in each chamber, such as a voltage differential between wells of the chamber attracts proteins of particular charges and that is applied by the electrical circuitry 110. As previously described, each chamber can be divided into three or more wells in specific embodiments, with a positive voltage and a negative voltage applied to two of the (secondary) wells and the third well being grounded. The electrical circuitry 110 is used to monitor nanopores of the chambers 106 for a change in ionic current across the nanopores which indicates a protein has traversed through. In response, the fluidic access circuitry 108 can close fluidic access to the bottom wells (e.g., that the protein is isolated in) and flush out the top well to remove any remaining sample. The fluidic access circuitry 108 can additionally flow a protease to the top well of the chambers 106 via the flow channels 104 and the proteins are driven to traverse the nanopore via the electric potential applied by the electrical circuitry 110 (e.g., voltage differential). The electric potential drives the proteins to the top wells and exposes the proteins to the protease. After exposure, an opposite electric potential is applied by the electrical circuitry 110 to drive translocation of the peptide fragments to the one or more bottom wells (or laterally, in some embodiments). The translocation can be repeated to increase an accuracy of the count and the protein/peptide fragments can be exposed to more than one protease to identify the protein and/or quantify an amount of the protein in the sample.

Figure 2A:
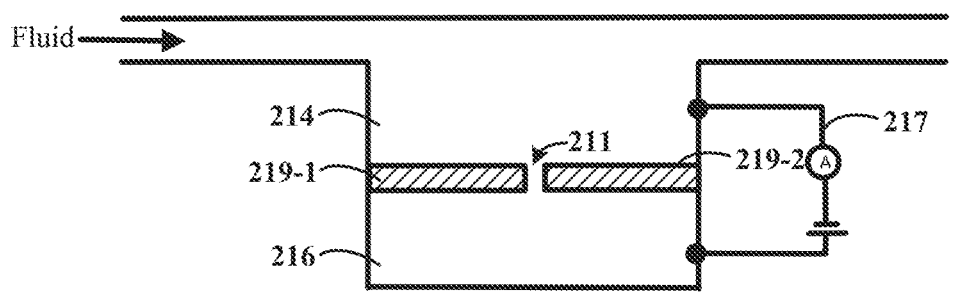
FIGS. 2A-2C illustrate example chambers of an apparatus, in accordance with various embodiments.
Figure 2B:
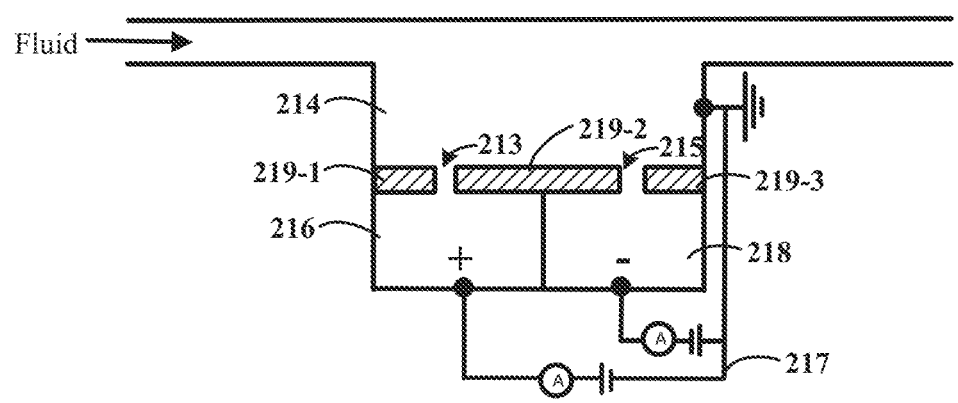

FIGS. 2A-2B illustrate example chambers of an apparatus, in accordance with various embodiments. As previously described, each chamber of the apparatus can include at least a first well and a second well separated by a membrane with a nanopore that provide fluidic communication between the wells. In various specific embodiments, the each chamber includes at least a first well, a second well, and third well. The nanopore can be of a size such that a single protein can translocate there through without allowing simultaneous passing of a second single protein or such that simultaneous passing of the first and second single proteins occurs at below a threshold frequency (e.g., is unlikely to occur or occurs infrequently). In some specific embodiments, the nanopore be of a size that a folded (or whole) protein cannot translocate. For example, the nanopore can be 1-50 nm in diameter. The chambers can have dimensions on the micron range, such as 50 nm-500 μm (e.g., 100 μm in each dimension in a specific embodiment). The membrane can be formed of SiN and the chamber (e.g., the walls forming the chambers) are formed of $SiO_2$, although embodiments are not so limited and the membrane can be formed of other oxides and other types of materials. For the fluidics and chambers, a variety of types of material can be used for microfluidics including hard and soft material. Example hard materials can include different types of glass, pyrex, quartz, fused silica, nitrides, oxides, etc. Example soft materials can include polymers, and epoxies such as SU-8, polydimethylsiloxane (PDMS), and poly(methyl methacrylate) (PMMA). Teflon can also be used in various embodiments. For the membranes which contain the nanopore, examples of other materials used to form the membranes can include hafnium oxide, aluminum oxide, titiania, silicon nitride, silicon dioxide, amorphous silicon, graphene, and boron nitride, among other materials.

FIG. 2A illustrates a specific example of a chamber 205. As illustrated the chamber 205 is in fluidic communication with one or more fluidic channels used to flow the sample. The chamber 205 includes a first well 214 that is separated from a second well 216 by a membrane 219-1, 219-2. The membrane 219-1, 219-2 has a nanopore 211 formed therein that provides fluidic communication between the first well 214 and the second well 216. Each of the first and second wells 214, 216 are electrically addressed via electrical circuitry 217.

FIG. 2B illustrates another specific example of a chamber 207. Similar to FIG. 2A, the chamber 207 is in fluidic communication with one or more fluidic channels used to flow the sample. The chamber 207 includes a first well 214 that is separated from a second well 216 and a third well 218 by membranes 219-1, 219-2, 219-3. The membranes 219-1, 219-2, 219-3 have nanopores 213, 215 formed therein that provide fluidic communication between the first well 214 and the second well 216 and fluidic communication between the first well 214 and the third well 218. Each of the first, second and third wells 214, 216, 218 are electrically addressed via electrical circuitry 217.

In the embodiments illustrated by FIGS. 2A-2B, a solution is flown through the fluidic channels across the top and bottom of the substrate to fill the chambers, which are oriented along the plane of the substrate. The top fluidic channels feed the first well 214 in each chamber and the bottom fluidic channels feed the second and/or third wells 216, 218 in each chamber. Once the nanopores are formed, fluid can enter on the top of the substrate, flow to the top well of a chamber, flow through the nanopore in a suspended membrane, pass into the bottom well of a chamber, and exit through the bottom microfluidics (or vice versa).

Figure 2C:
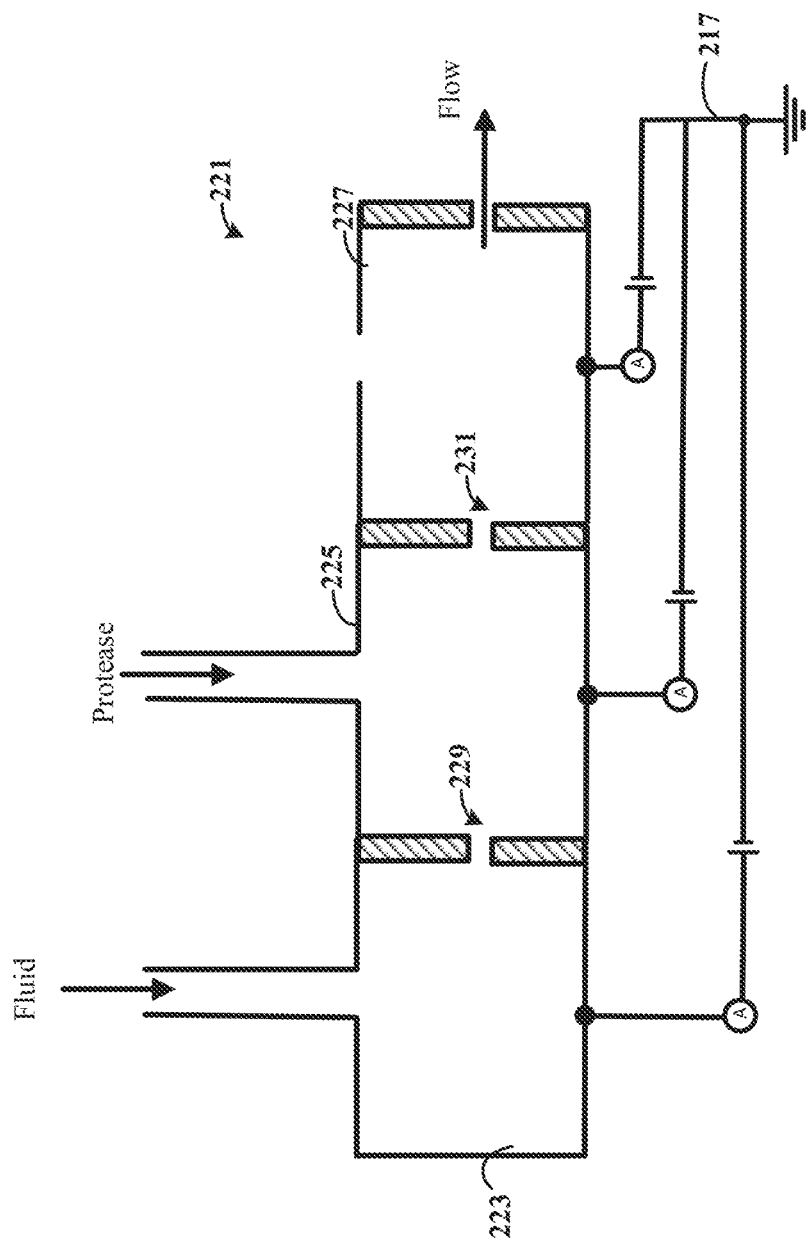

FIG. 2C illustrates another example chamber. In various embodiments, a chamber includes a plurality of wells with membranes that are arranged normal to the plane of the substrate, such that fluid flowing through the nanopores passes along the plane of the substrate rather than from top to bottom as illustrated by the chambers of FIGS. 2A-2B. The chamber 221 includes a plurality of wells 223, 225, 227. For example, the first well 223 is separated from the second well 225 by a membrane having a first nanopore 229 and the second well 225 is separated from the third well 227 by a membrane having a second nanopore 231. The first and second nanopores 229, 231 are used to provide fluidic communications between the wells 223, 225, 227. Each of the first, second and third wells 223, 225, 227 are electrically addressed via electrical circuitry 217.

As described above, the fluid flowing through the nanopores 229, 231 passes along the plane of the substrate. The proteases can be immobilized to a surface inside a respective well or flow into a respective well, in such an embodiments. Although the embodiment of FIG. 2C illustrates three wells forming a chamber, embodiments described herein are not so limited.

In each of the chambers illustrated by FIGS. 2A-2C, the apparatus uses information on protein concentration delivered from a pre-processing module or unit as input to a feedback loop that can be used to determine how long to continue washing the protein solution across the chambers containing nanopores based on the number of translocation events into the chambers, and in order to give the chambers the opportunity to trap a threshold fraction of proteins. The pre-processing module can include protease inhibitors that mitigate or prevent premature proteolysis, and/or a filter that removes sample components larger in diameter than a denatured protein. The pre-processing module can perform immunodepletion of common proteins (such as albumin) and/or fractionation by protein characteristics (e.g., protein size or some other characteristic).

Figure 3:
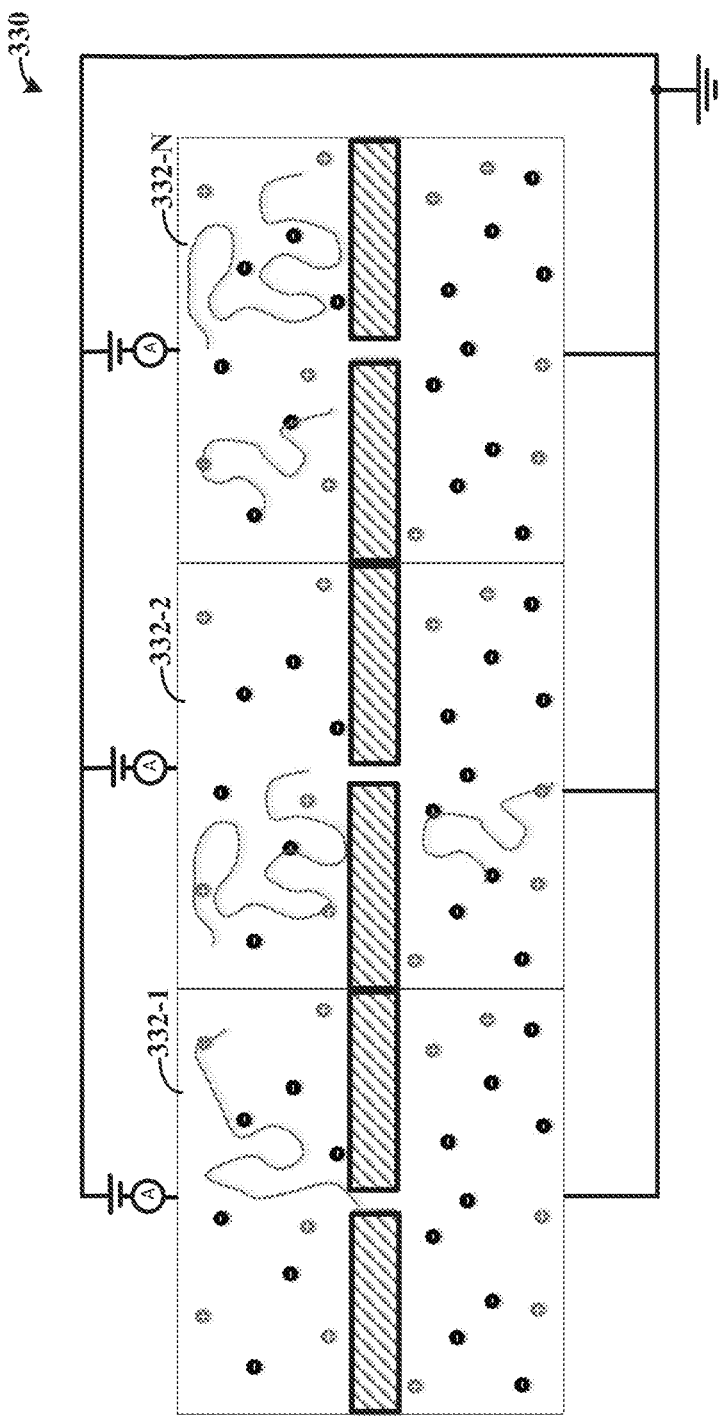
FIG. 3 illustrates an example of multiple chambers of an apparatus, in accordance with various embodiments.

FIG. 3 illustrates an example of an apparatus having multiple chambers, in accordance with various embodiments. The apparatus illustrated by FIG. 3 can include a microfluidic chip 330 having a plurality of chambers 332-1, 332-2, 332-N. The chambers 332-1, 332-2, 332-N can include or be configured as the specific chamber 205 or 207 illustrated by FIGS. 2A-2B. Each of the plurality of chambers 332-1, 332-2, 332-N are electrically addressable and used to isolate single (types of) proteins and evaluate the single (types of) proteins from a sample. The microfluidic chip 330 can be used to process multiple different types of proteins at one time and/or to identify concentrations of one or more protein types in the sample.

In various embodiments, the apparatus can include a plurality of different chambers, such as hundreds to millions of chambers, and which can be used to multiplexing purposes. For example, a sample can be analyzed to identify a plurality of different proteins and/or quantify an amount of each of the plurality of different proteins. Multiplexing can be used to a variety of purposes, such as diagnostic and forensic identification. By analyzing large numbers of panels at a time, more information can be gleamed than analyzing one to a few. For example, multiplexing can be used for typing of acute myeloid leukemia cell lines for disease outcomes and choice of chemo therapy. As another specific multiplexing example, consider a person with rheumatoid arthritis. A doctor takes a blood sample and cultures immune cells from the blood sample. The sample is pre-processed to enrich and/or purify the proteins. The apparatus can be used to inventory proteins of single cells and to test drug effects thereon. For example, a first drug may be deemed ineffective, a second drug may have side effects, and the third drug may be deemed successful.

Figure 4B:
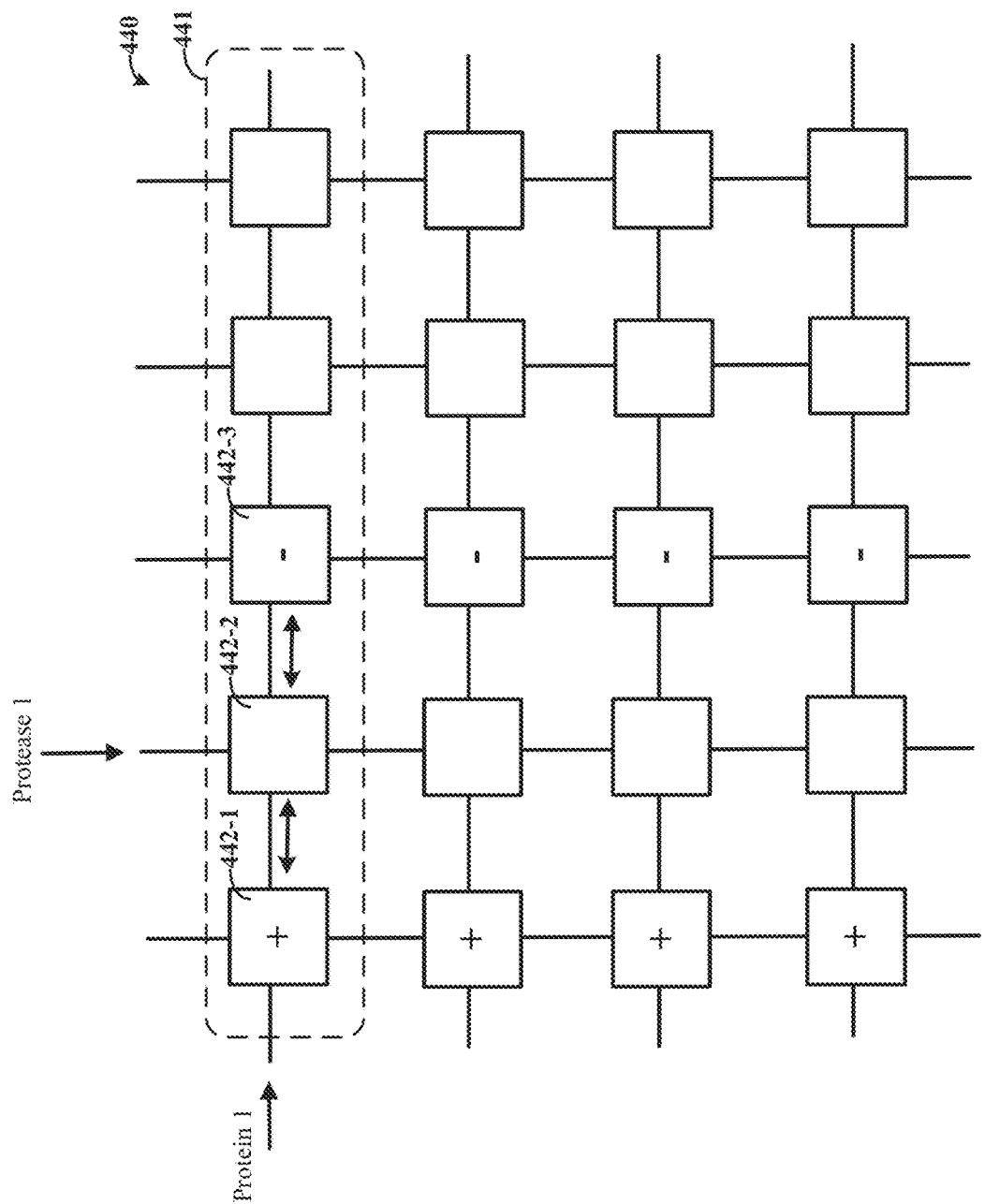

FIG. 4A-4B illustrate an example of an apparatus having multiple chambers, in accordance with various embodiments. The apparatuses illustrated by FIGS. 4A-4B can include a microfluidic chip 440 having a plurality of chambers. The chambers can be in accordance with the specific chamber 221 illustrated by FIG. 2C. Each of the chambers is represented by a row of the microfluidic chip 440 as illustrated by FIGS. 4A-4B, and each row represents an experiment run on a single protein (e.g., single type of protein or single unique protein). Using the top row as an example, the chamber 441 includes a plurality of wells 442-1, 442-2, 442-3, 442-4, 442-5 arranged in a lateral direction with respect to one another. However, as may be appreciated the microfluidic chip can be oriented differently, such that a chamber includes a vertical column of wells. Each of the plurality of wells 442-1, 442-2, 442-3, 442-4, 442-5 of the chamber 441 have a membrane there between with a nanopore used to provide fluidic communication. Additionally, each of the wells 442-1, 442-2, 442-3, 442-4, 442-5 has the buffer solution that contains free ions, as previously described and which can be provided via respective fluidic channels.

As illustrated by the specific embodiment of FIG. 4A, fluidic feeds are provided by fluidic channels in the north/south direction and the nanopores are in the east/west directions. The fluidic channels in the north/south direction, e.g., 443, 445, 447, can be selectively opened and closed, such as by fluidic access circuitry. In a specific embodiments, the sample is flown through the first fluidic channel 443 for capture of single proteins in the second column, e.g., the second well 442-2 of the chamber 441. A single protein is captured by selectively translocating the protein laterally to the second well 442-2 and a first protease is flown in the second well 442-2 via the second fluidic channel 445. After the exposure to the first protease, peptide fragment translocation events can be detected through at least one nanopore between the second well 442-2 and a third well 442-3, and optionally between the second well 442-2 and the first well 442-1, as further described herein. After counting translocation events, and optionally repeating the detection of translocation events to increase accuracy, the peptide fragments are translocated to the fourth well 442-4 for exposure to a second protease. After the exposure, translocations of peptide fragments can be detected through at least one nanopore between the fourth well 442-4 and a fifth well 442-5, and optionally between the fourth well 442-4 and the third well 442-3, as further described herein and which can be repeated to increase the accuracy of the count. The second protease can be flown to the fourth well 442-4 via the third fluidic channel 447. In other embodiments, the first and second proteases can be immobilized inside the respective second well 442-2 and fourth well 443-4.

Each of the respective wells are electrically addressable. FIG. 4B illustrates a particular example of electrically addressing the first well 442-1 and the third well 442-3 for translocating peptide fragments between the second well 442-2 and one or more of the first and third wells 442-1, 442-3 after exposure to the first protease. The second well 442-2 can be grounded while the first well 442-1 has a positive voltage applied and the third well 442-3 has a negative voltage applied, and which generates the voltage differential between the first, second and third wells 442-1, 442-2, 442-3. The positive and negative voltages can be used to respectively attract negatively charged and positively charged peptide fragments, and which can be used to ascertain a charge for each of the peptide fragments (and the protein as a whole after one or more proteolysis). The number of columns of the chambers can be determined by the number of proteolysis steps. For example, the column total can be defined by: (the number of proteases times two) plus one.

Figure 5A:
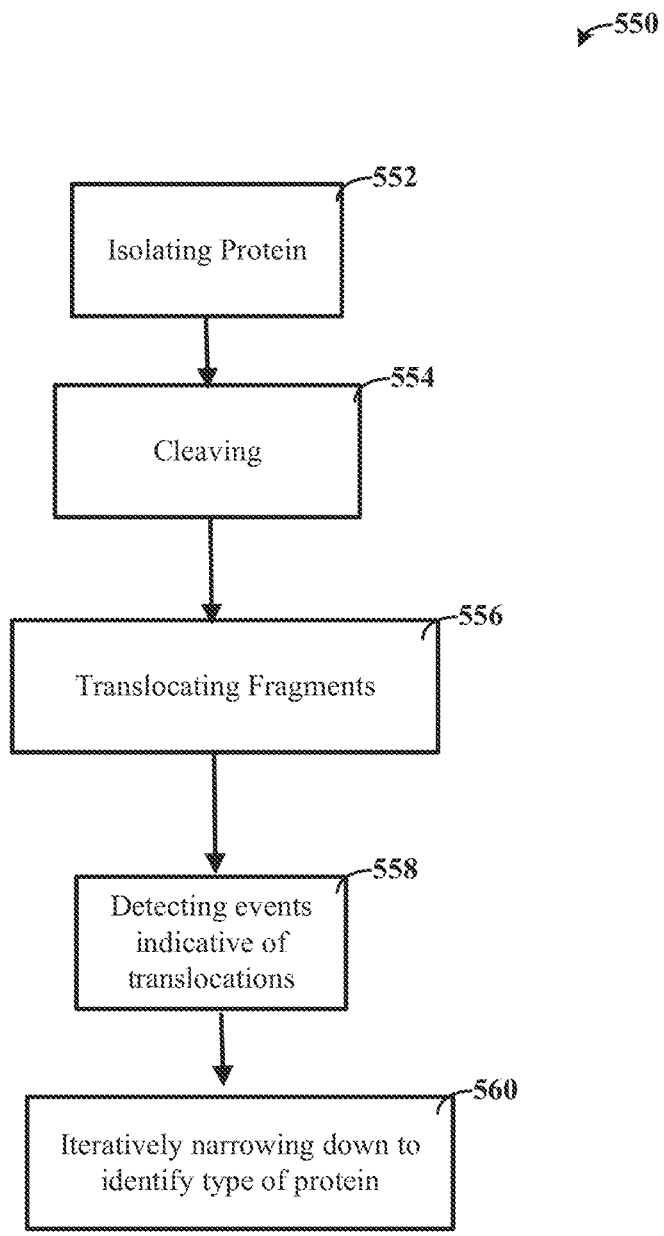
FIGS. 5A-5B illustrate example methods for detecting events related to translocation of protein fragments through a nanopore, in accordance with various embodiments.
Figure 5B:
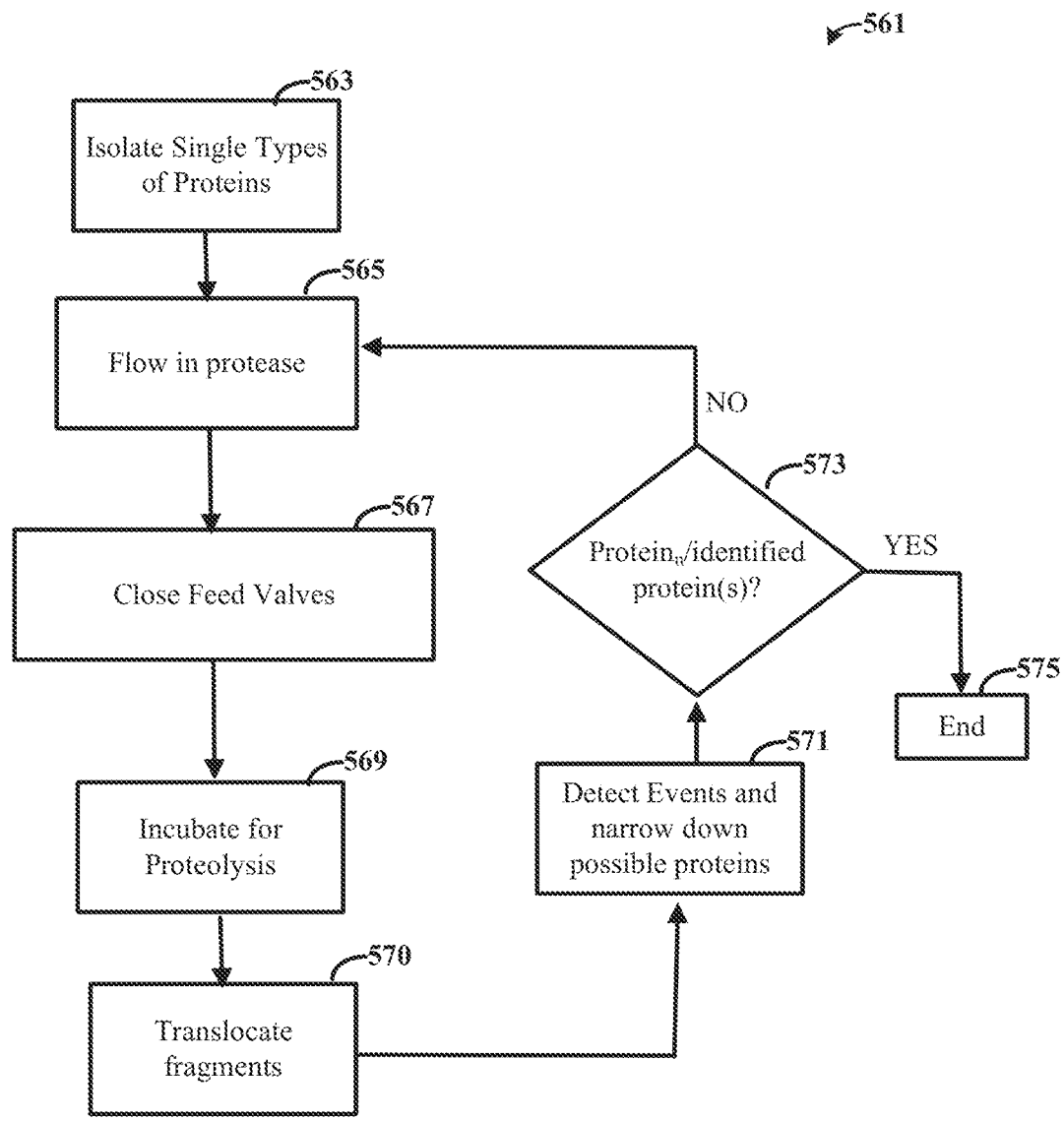

FIGS. 5A-5B illustrate example methods for detecting events related to translocations of peptide fragments through a nanopore, in accordance with various embodiments. The above described apparatuses having one or more chambers can be used for evaluating unknown proteins in a sample, via a proteolysis process, such as the methods illustrated by FIGS. 5A-5B.

FIG. 5A illustrates an example method for evaluating a single protein in a sample. The method 550, at 552, includes isolating a single protein from a sample in a chamber having at least a first well and a second well separated from the first well by a membrane with a nanopore. The nanopore, as previously described, provides fluidic communication between the first and second wells. The isolation can occur by creating a voltage differential between the first and second wells (e.g., applying a voltage to the second well, which is opposite side of the membrane as the sample is flown), and detecting translocation of a single protein based on changes in ionic current through the nanopore. In response to the changes in ionic current, the voltage differential can be removed (e.g., discontinue the voltage applied to the second well). By removing the voltage differential, another single protein can be prevented from (or mitigated) translocated to the second well. In various embodiments, after isolating the single protein, the chamber is isolated from fluidic access to the remainder of the sample, as further described in connection with FIG. 5B and illustrated further herein.

At 554, the method 550 further includes cleaving the single protein into a plurality of peptide fragments via exposure to a protease in the first well. Exposing the single protein to the protease can include translocating the single protein from the second well to the first well by generating the voltage differential there between and discontinuing the voltage differential in response to translocation. The single protein can be exposed to the protease for a period of time, such as a time sufficient to allow for cleaving. In various embodiments, the proteases are flown into the first well via selective access by the fluidic access circuitry. The protease can be bound to a surface, such as bound to beads or bound to a surface of the well. For example, the proteases are attached (e.g., anchored) to beads to mitigate translocation and/or denaturation. The proteases attached to the beads can allow for ease of separation. More specifically, the flow in protease attached to magnetic beads are flown into the first well and the separated from proteins using a magnet. Although embodiments are not so limited, and in other embodiments, the proteases can be attached to chamber walls.

At 556, the method 550 includes translocating the plurality of peptide fragments through the nanopore by applying an electric potential across the nanopore(s) in the chamber after cleavage of the single protein by the protease. In specific embodiments, the electric potential induces an electric field and/or imparts an electrophoretic force that is generated by applying the electric potential across the nanopore(s). While the electric field imparts an electrophoretic force on charged fragments, in specific embodiments, additional forces can be applied, such as a pressure-induced force on the fluid flowing through the nanopore which can influence the fragment motion.

At 558, the method 550 includes detecting events indicative of the translocations of the plurality of peptide fragments cut from the single protein through the nanopore and to the second well. The detected events include changes in ionic current through the nanopore, such as an ionic current depression caused by the respective peptide fragment(s) blocking current while traversing through the nanopore.

Although not illustrated, the detected events can be used to evaluate the protein. For example, the method 550 can include determining an estimated number of a particular target cleavage site within the single protein based on the detected events. The number of translocations, determined by the detected events, can be correlated with a percentage of a specific target cleavage site. As previously described, proteases split peptide bonds at the target cleavage sight in the particular single protein and/or resulting peptide fragments (e.g., a cut between two amino acids and the shorter peptides can be counts). As a specific example, a particular protease may split peptide bonds between cysteine and threonine, and the number of detected events are indicative of the number of pairs of cysteine and threonine. The estimated number of a specific target cleavage site can be based on cleavage rules specific to the protease and/or to each protease.

In a number of specific embodiments, the method 550 further includes, at 560, narrowing down the identity of the single protein by iteratively introducing additional proteases and correlating the number of translocations with a number of the target cleavage sites (including cleavage errors). The iterative process can include iteratively exposing the single protein/the peptide fragments to a plurality of proteases and counting detected events after each exposure. For example, the single protein can be sequentially exposed to each of a plurality of a different proteases and the method 550 further includes determining numbers of peptide fragments derived from the exposure to each of the plurality of different proteases. The single protein sequence can be identified, with a confidence value, based on estimated numbers of amino acids in the single protein determined using the detected events and a bioinformatics model (e.g., the cleavage rules and non-idealities, as previously described and further described herein. Further, an estimate of the length of the translocated protein and/or peptide fragments can be provided based on a measure of a duration of each the detected events.

In various embodiments, each chamber includes three or more wells and can be used to determine a sign of net charge of peptide fragments. For example, the chamber includes the second well and a third well (e.g., lower or secondary wells) separated from the first well by membranes and in fluidic communication with the first well by respective nanopores. In such embodiments, the method 550 further includes, after cleaving the single protein, applying a first polarity (e.g., positive) voltage to the second well and applying a second polarity (e.g., negative) voltage to the third well, and detecting changes in ionic current through the nanopores, which are indicative of translocation of one of the plurality of peptide fragments cut from the single protein to the second and/or third wells. The number of positively and negatively charged peptide fragments cut from the single protein can be determined based on the number of detected changes in the ionic current through each respective nanopore. And the charges can be used to determine a net charge of the single protein and/or to refine identification of the protein (e.g., increase a confidence value).

In various embodiments, as further illustrated and described by FIG. 5B, the method can be applied to isolate and identify a plurality of types of proteins in the sample. FIG. 5B illustrates an example method used to isolated plurality of single types of proteins in a sample in a plurality of different chambers. For example, a microfluidic chip can include a plurality of chambers, each of the plurality of chambers having at least a first well and a second well separated from the first well by a membrane with a nanopore. The method 561 includes detecting events after cleaving each of the plurality of single types of proteins in each respective chamber via exposure to the protease and driving translocation.

At 563, the method 561 include isolating single types of proteins in respective chambers of the apparatus. In various embodiments, the sample is flown across the chambers until at least a threshold number of the chambers have an isolated single type of protein. The fluidic access circuitry can close fluidic access to the chamber(s) in response to detecting the at least threshold number of chambers have an isolated single type of protein (e.g., responsive to detecting the changed ionic current through at least a subset of nanopores). In various embodiments, as further illustrated herein, prior to flowing the sample, a solution containing dissolved salts, surfactants, buffers, among other constituents is flowed into the apparatus such that every chamber and well is filled with the solution.

At 565, the proteases can be flown into the chambers on the opposite side of the membrane as the proteins are located. Although embodiments are not so limited, and in some instances, the proteases can be immobilized to a surface of a well to which the proteins are not yet exposed. In some embodiments, the solution can be exchanged for another solution.

At 567, the fluidic feed valves, which are used to flow in the proteases, are closed to isolate the chambers. The proteins are then driven to the protease side of the membrane and incubated with the protease, at 569. For example, a single type of protein and protease are held in the same well of a chamber with no applied voltage for some amount of time to allow for the protease to cleave the protein into fragments.

At 570, the resulting peptide fragments are translocated through one or more nanopores. For example, the resulting peptide fragments are driven away from the proteases, through the nanopore(s), and to the opposite side of the membrane(s) by applying one or more voltages. The wells can be subdivided to collect and separate fragments based on net charge. The ionic current of each nanopore is measured during this process, as described above. The number of blocked current events are detected, at 571, which corresponds with the number of peptide fragments generated by the proteolysis and which is related to the number of target cleavage sites present in the original protein. Voltage bias across the nanopore can be reversed to change the translocation direction, enabling the same collection of peptide fragments to be driven through the nanopore(s) multiple times to provide a more accurate peptide count.

In various embodiments, the single nanopores can be exposed sequentially to more than one protease to identify the protein or to rule out a particular protein. For example, at 573, the method 561 includes determining if the proteins have been exposed to N number of proteases, e.g., protease$_N$, and/or if the particular protein has been identified (or effectively ruled out as being in the sample). If so, the process can end at 575. If not, the steps of flowing in a protease at 565, closing feed valves 567, incubating 569, translocating 570, and detecting events 571 are repeated. Although the method 573 illustrates a decision at 573, in various embodiments, the method 561 may automatically repeat the exposure to N number of proteases and does not include such a determination.

As described above, the various apparatuses and methods of using the apparatus involve translocations of single types of proteins and/or peptide fragments which are driven by the electric field. The protein and peptide fragments can be repetitively and selectively driven back and forth between the wells via the selective application of the electric potential (generating an electric field) and/or a direction of bias. Additionally, each count after proteolysis can be repeated one or more times prior to exposure to another protease or otherwise finalizing the count, in order to increase a statistical accuracy of the count.

Figure 6:
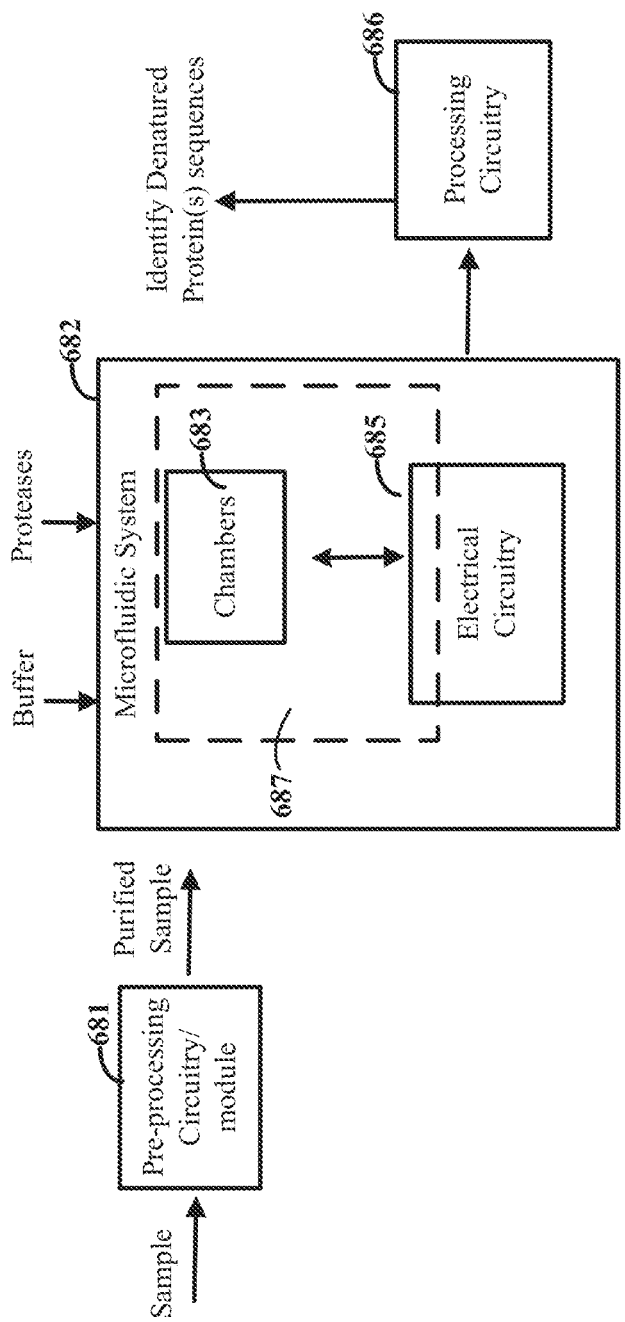
FIG. 6 illustrates an example method of processing a sample, in accordance with various embodiments.

FIG. 6 illustrates an example method of processing a sample, in accordance with various embodiments. As previously described, an input sample can be pre-processed by a pre-processing module 681. The pre-processing module 681 can include circuitry for interfacing with a sample loading apparatus and producing purified protein solution with a level of contaminants at or below a threshold tolerance of the apparatus. Two types of contaminants include non-protein and protein contaminants. Non-protein contaminants can be filtered out or pulled out during sample processing and/or purification. Non-protein contaminants can pose a risk for clogging nanopores and/or for extraneous translocation signals. While non-protein contaminants are not cleaved by the protease, non-protein contaminants can cause errors in fragment counting. Protein contaminants are the wrong protein in a pool of purified proteins. The protein contaminants may be cleaved by the protease, and can introduce errors to the fragment count. The threshold tolerance of the apparatus is a function of the number of initial purified proteins being analyzed. Self-cleaving between proteases can also occur, causing additional contaminants. The pre-processing module 681 breaks apart protein multimers and denatures proteins by mixing with a buffer containing denaturants, such as salt and urea. The preprocessing reduces proteins by breaking disulfide bonds (e.g., by mixing with a buffer containing a reducing agent, such as TCEP). Further, the pre-processing module 681 can quantify protein concentration of the sample, which is input to the microfluidic system 682, and can be quantified via optical spectrometry. The pre-processing module 681 delivers the purified and protein solution to the microfluidic system 682.

The microfluidic system 682, as previously described, includes a microfluidic chip 687 and portable circuitry used to evaluate proteins in the sample. The microfluidic chip 687 includes the substrate having the fluidic channels and plurality of chambers 683. The microfluidic system 682 further includes electrical circuitry 685, at least part of which is on the microfluidic chip 687 and used to detect events and drive translocations. As also illustrated, input channels are used to flow a buffer solution into the chambers 683 and, optionally, to flow a solution containing proteases.

As illustrated and described above, the electrical circuitry 685 provides electrical current and/or amplifies ionic current and is located locally on the microfluidic chip 687 to address each chamber individually and globally and/or externally to implement decisions for the microfluidic system 682 as a whole.

The local electronic component can implement an electroporation procedure for nanopore formation, ramping the voltage across each membrane until a threshold ionic current is detected and subsequently conducting any nanopore conditioning sequences that may be implemented to create a stable ionic flow through the nanopore. The local electronic component can further implement a nanopore validation procedure and can permanently turn off driving voltages for a chamber if a nanopore does not meet metrics. For the initial capture, the local component turns off the driving voltage that enables translocation once a single protein (e.g., single type of protein) passage is detected. Additionally, the local electronic component can transform raw ionic current signals into counts, detect clogging events (blocking of a nanopore lasting longer than a pre-determined time period), initiate unclogging procedures, detect complete passage of all fragments (as determined by time since last translocation), initiate recount (by reversing driving voltage), and/or or notify the full-system control module (e.g., processing circuitry 686) that chamber is ready for next proteolysis cycle.

The global electronic component can receive translocation counts from each individual chamber and compiles these as inputs to bioinformatics model, interface with a database on protein sequence and based on presumed species under measurement, and initiate the next proteolysis cycle based on quorum of individual chamber readiness. In various embodiments, the global electronic component includes processing circuitry 686 which may be part of or separate from the microfluidic system 682.

The microfluidic chip 687 can contain the array of chambers (e.g., single molecule traps) and can be a consumable. This chip 687 can interface with non-consumable fluidic inputs and with a non-consumable substrate that addresses the electronic control and amplification requirements of each chamber 683 separately through a magnetic or other type of alignment.

In other embodiments, the microfluidic chip 687 containing the array of single molecule traps and cell-specific elements of the electrical circuitry 685 is a consumable. This chip can interface with non-consumable fluidic inputs and a non-consumable global connection to electronic control and amplification hardware (e.g., electrical circuitry 685 and/or processing circuitry 686).

Figure 7A:
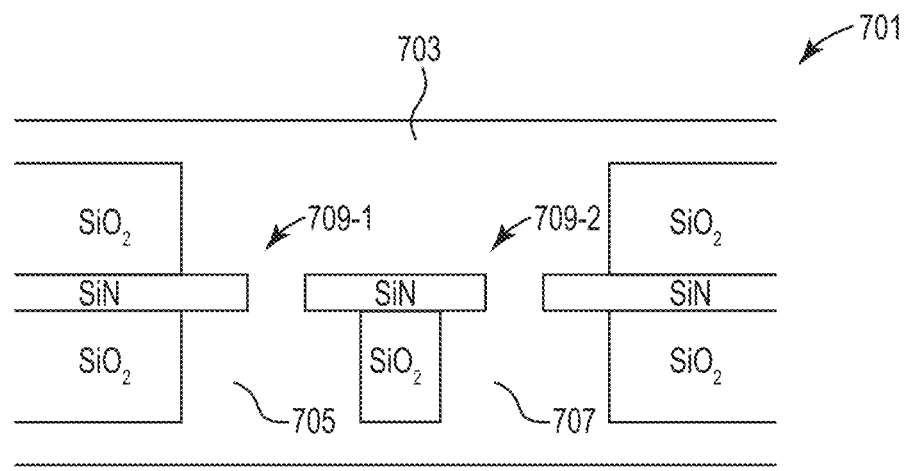

FIGS. 7A-7E illustrate various example apparatuses, in accordance with various embodiments. The apparatuses illustrated by FIGS. 7A-7E can include chambers in accordance with the specific chamber 205 or 207 illustrated by FIGS. 2A-2B. As illustrated by FIG. 7A, the chamber 701 includes a first well 703 separated from a second well 705 and a third well 707 by membranes. The membranes are formed of SiN, and the walls of the wells 703, 705, 707 can be formed by $SiO_2$, however the embodiments are not so limited. The membranes include a first nanopore 709-1 and a second nanopore 709-2.

Figure 7B:
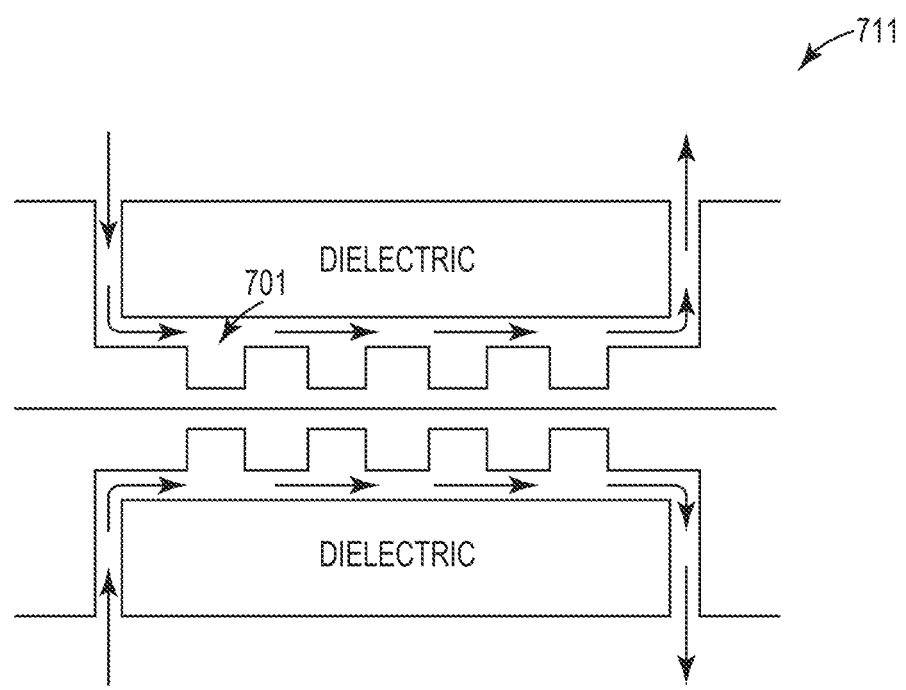

As illustrated by FIG. 7B, an apparatus 711 can include a plurality of chambers, which are similar to the chamber 701. A solution is flown through the fluidic channels across the top and bottom of the substrate to fill the plurality of chambers, which are oriented along the plane of the substrate. The top fluidic channels feed the first well in each chamber and the bottom fluidic channels feed the second and/or third wells in each chamber. Once the nanopores are formed, fluid can enter on the top of the substrate, flow to the top well of a chamber, flow through the nanopore in a suspended membrane, pass into the bottom well of a chamber, and exit through the bottom microfluidic chip (or vice versa).

Proteases are introduced sequentially into wells on one side of the substrate and washed away once used. In such examples, the timing of introduction of new proteases is set by the empirically determined time required to complete a proteolysis and measurement cycle.

Figure 7C:
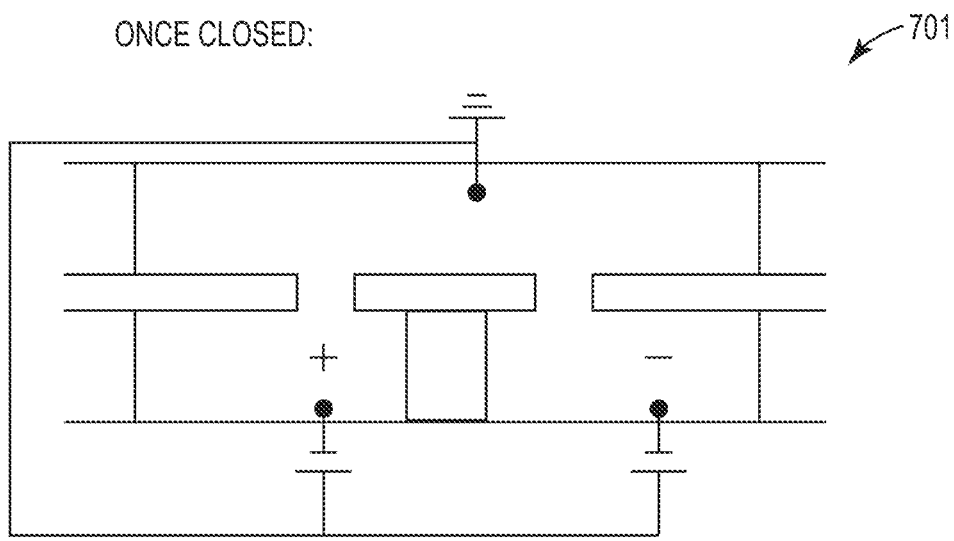

As illustrated by FIG. 7C, fluidic access can be closed to the chamber 701 and different voltages can be applied to the different chambers. FIGS. 7D-7E illustrate an example of opening and closing fluidic access to the chambers. As illustrated, the microfluidic chip can include a dielectric layer 720 (e.g., a flexible dielectric material such as an electroactive polymer). The dielectric layer 720 can transition or move between an open-fluidic-access state (e.g., is compressed), as illustrated by FIG. 7D, to a closed-fluidic-access state (e.g., expanded) as illustrated by FIG. 7E. The open-fluidic-access state can allow for fluidic access to the chambers (e.g., chamber that includes the well 703) and the closed state can block access.

Although embodiments are not so limited and fluidic access can be provided and blocked in a variety of ways. For example, FIGS. 8A-10 illustrates other example ways.

FIGS. 8A-8B illustrate an example of closing fluidic access to chambers, in accordance with various embodiments. In such an example, pressure is used to block each of the chambers. For example, FIG. 8A illustrates no pressure applied to fluidic channels, and in which fluidic access to the chambers is provided. FIG. 8B, by contrast, illustrates pressure applied, and which blocks fluidic access to the chambers.

FIGS. 9A-9B illustrate an example of closing fluidic access to chambers, in accordance with various embodiments. In such an example, access is selectively provided and blocked to the chambers, as illustrated by FIGS. 9A and 9B.

Figure 10:
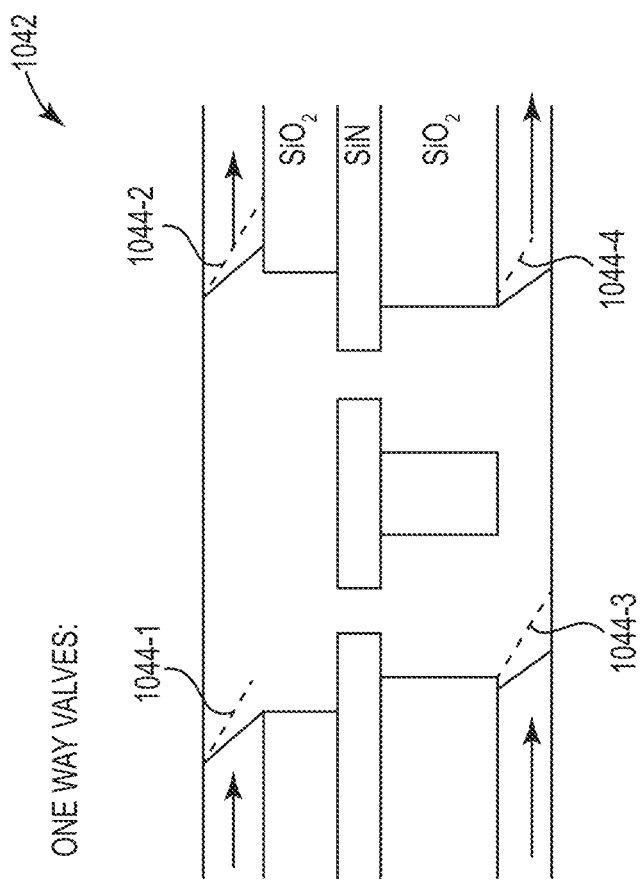
FIG. 10 illustrates an example of closing fluidic access to chambers, in accordance with various embodiments.

FIG. 10 illustrates another example of closing fluidic access to chambers, in accordance with various embodiments. In such embodiments, fluidic access is provided to the chamber 1042 via a plurality of valves 1044-1, 1044-2, 1044-3, 1044-4 that provide fluidic access to both the top and bottom fluidic feeds.

FIGS. 11A-11E illustrate an example process of detecting events related to translocations of peptide fragments through a nanopore, in accordance with various embodiments. Although not illustrated, a solution which may contain dissolved salts, surfactants, buffers, among other constituents, is flowed into the microfluidic chip such that every chamber and well is filled with solution.

Figure 11A:
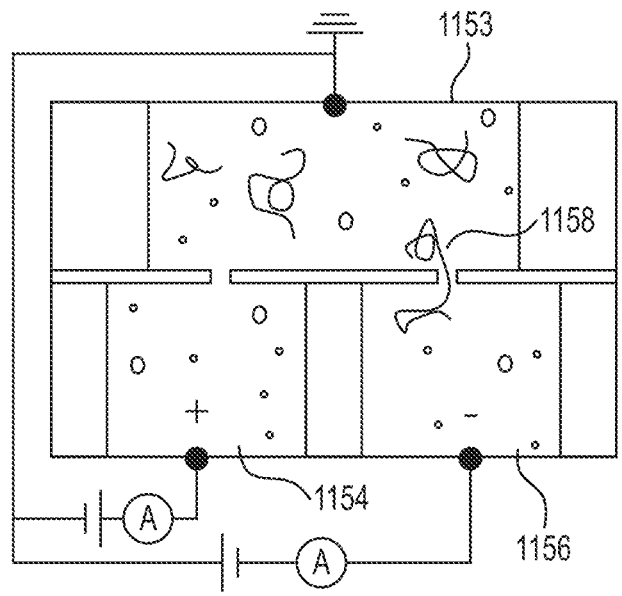
FIGS. 11A-11E illustrate an example process of detecting events related to translocation of protein fragments through a nanopore, in accordance with various embodiments.
Figure 11B:
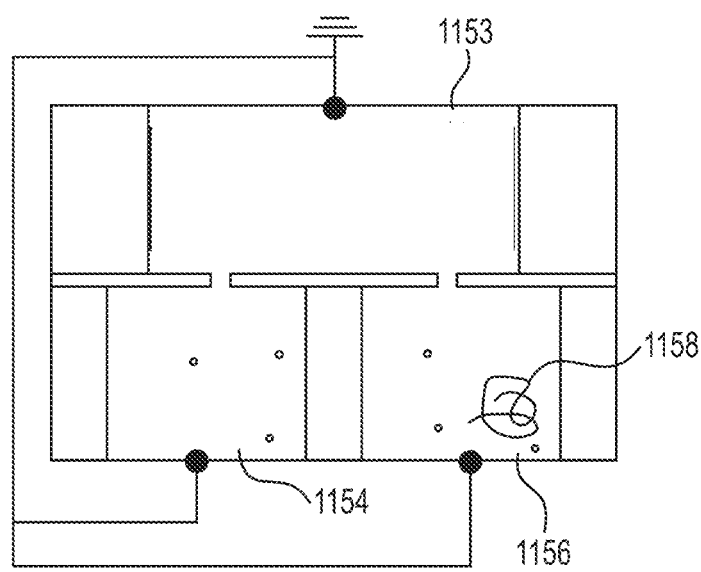

As illustrated by FIG. 11A, a sample containing a mixture of proteins is flown into the chambers, while a positive and/or negative voltage is applied to one of the (secondary) wells in each chamber which is on an opposite side of the membrane as the sample. In the specific embodiment of FIG. 11A, the first well 1153 is set to ground, a positive voltage is applied to the second well 1154, a negative voltage is applied to the third well 1156. Proteins in the sample with a net charge can experience an electrophoretic force and are drawn from one side of the membrane, to the other, through the nanopore, also herein referred to as translocation. In a number of embodiments, the single protein 1158 translocates through the nanopore to the third well 1156, as illustrated by FIG. 11B. The single protein 1158 can be estimated to have a positive net charge. The ionic current through the nanopore is measured during the process. When the single protein 1158 translocates through the nanopore, the ionic current is blocked resulting in an ionic current depression. In response, the voltages applied to the wells 1154 and 1156 are turned off to prevent or mitigate further protein translocation.

Figure 11C:
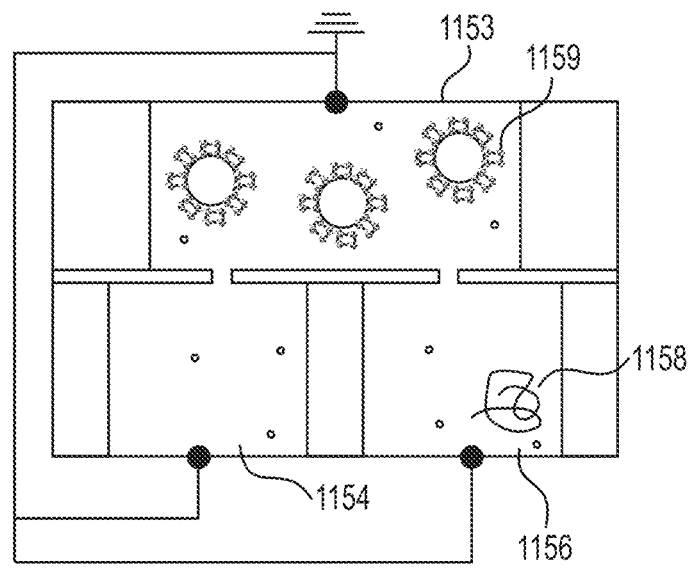

The sample can be flown through the microfluidic chip a number of times, such that a threshold number of single proteins are captured from the sample and trapped in chambers. Once a threshold number of proteins are trapped, proteolysis can begin. As may be appreciated the concentration of protein(s) can be determined prior to the above-described procedure using standard techniques known in the art. For example, as illustrated by FIG. 11C, a first protease 1159 is flown in solution through the fluidic channels feeding the chambers and to the first wells (e.g., first well 1153) that are on an opposite side of the membrane as the trapped proteins. The protease may be optimized for solution conditions that are different from those used for electroporation or protein capture. For example, the first protease 1159 is illustrated as immobilized on beads (e.g., a plurality of the first protease 1159 are attached to a bead and a plurality of beads are provided). Immobilizing proteases on beads can be used to control the exposure to the proteases as the proteases cannot traverse through the nanopore.

Figure 11D:
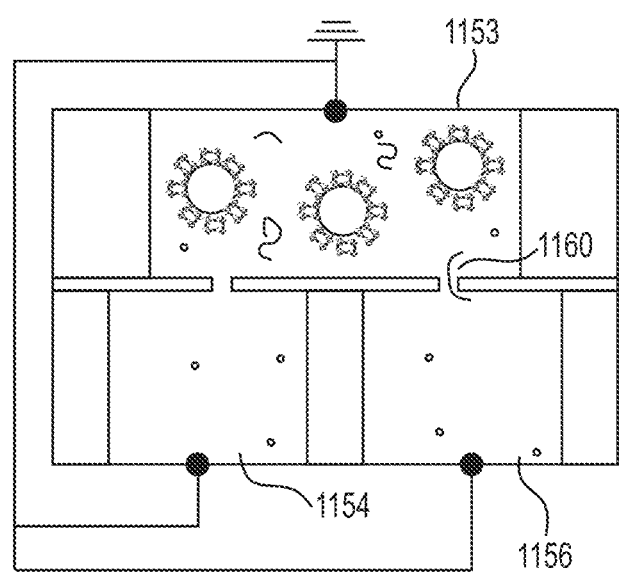

As illustrated by FIG. 11D, the single protein (e.g., protein 1158 illustrated by FIG. 11C) is driven with an applied voltage (e.g., a negative voltage applied to the first well 1153) to the first well 1153 containing the protease 1159. The charge of the voltage applied, in some specific embodiments, can be based on the estimated net charge of the single protein 1158. The protein blocks a portion of the ionic current through the pore during its passage, giving an indication to the electronic control system (e.g., the processing circuitry) that it has translocated. Though translocation signatures vary depending on details of protein/pore interaction, detection of translocation events (counting) is a high signal-to-noise measurement. The protease cleaves the single protein 1158 into a plurality of peptide fragments. As previously described, each protease cleaves proteins at specific target cleavage sites. The protein and protease are held in the same chamber with no applied voltage for some amount of time to allow for the protease to cleave the protein into peptide fragments. The number of peptide fragments generated are determined by the abundance of the target cleavage sites and the kinetics of the reaction. Temperature of the fluids may be controlled to optimize proteolysis.

The resulting peptide fragments are driven away from the proteases, through the nanopore, and to the opposite side of the membrane by applying a voltage. For example, FIG. 11D illustrates a fragment 1160 translocating to the third well 1156. The wells can be subdivided to collect and separate fragments based on the sign of net charge, as previously described. The ionic current of each nanopore is measured during this process.

The number of blocked current events corresponds with the number of fragments generated by the proteolysis, which can be related to the number of target cleavage sites present in the original protein. Voltage bias across the nanopore can be reversed to changed translocation direction, enabling the same collection of peptide fragments to be driven through the nanopore times to provide better accuracy on peptide count.

Peptides can carry a net charge, and are expected to translocate through a nanopore biased appropriately for that net charge. In a dual-pore chamber, this property can be exploited to determine the sign of the net charge of each peptide fragment as well as the peptide count. Additionally, the duration of the detected events can be measured and used to provide an estimate of the length of the translocated protein and/or peptide fragment.

If a molecule clogs a nanopore, it can be ejected with no damage to the nanopore by applying an opposite voltage pulse from the original driving force. Once the protein or peptide fragment is ejected, the ionic current returns to its base level. An automated pore unclogging procedure can be implemented by defining a threshold (e.g., maximum) blocked current time, and when the nanopore is blocked for longer than that time, an automatic unclogging pulse is applied.

The steps illustrated by FIGS. 11A-11D can be repeated for a series of proteases. Each proteolysis step gives more information about what the original protein in each well is.

Figure 11E:
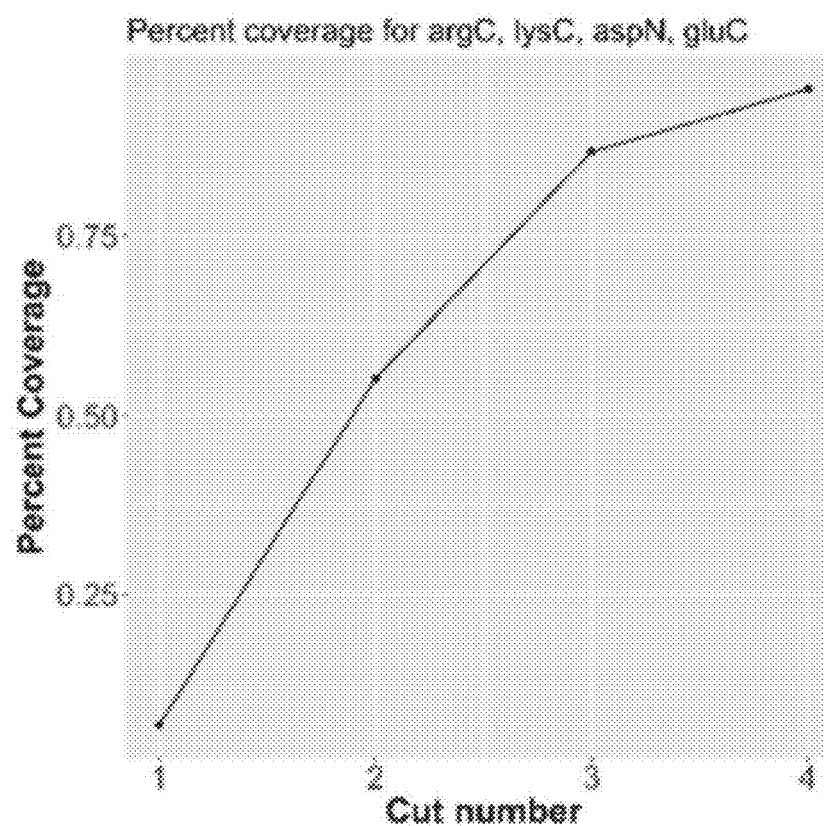

FIG. 11E illustrates example percentage of human proteins identified based on the number of proteases the sample is exposed to. As illustrated in the specific example of FIG. 11E, at least a threshold number of (human) proteins are identified in response to exposure to argC, lysC, aspN, and gluC.

More Detailed/Experimental Embodiments

Embodiments in accordance with the present disclosure can be used to explore and identify protein(s) in a sample at the single-molecular level. The proteins can be identified in minute samples, such as those left behind by a human fingerprint when DNA is not present. Such identification can be used to identify a person by law enforcement or the intelligence community. The protein identification can also be used to identify virulence factors at the single bacterium level and/or identify proteins expressed on the surfaces of single viruses, which can allow for researchers to predict what pathogens are likely to become common causes of disease and/or to produce vaccines for emerging pathogens. The ability to inventory proteins inside extracellular vesicles can be used to extend the power of liquid biopsies for cancer or other disease conditions. As another example, it can allow serum assays for proteins that are currently below the limit of detection of immunoassays, which can be used to identify human or animal health problems earlier and/or with greater accuracy. As the apparatus can be portable, the apparatus can be used to replace immunoassays carried by medics.

Figure 12A:
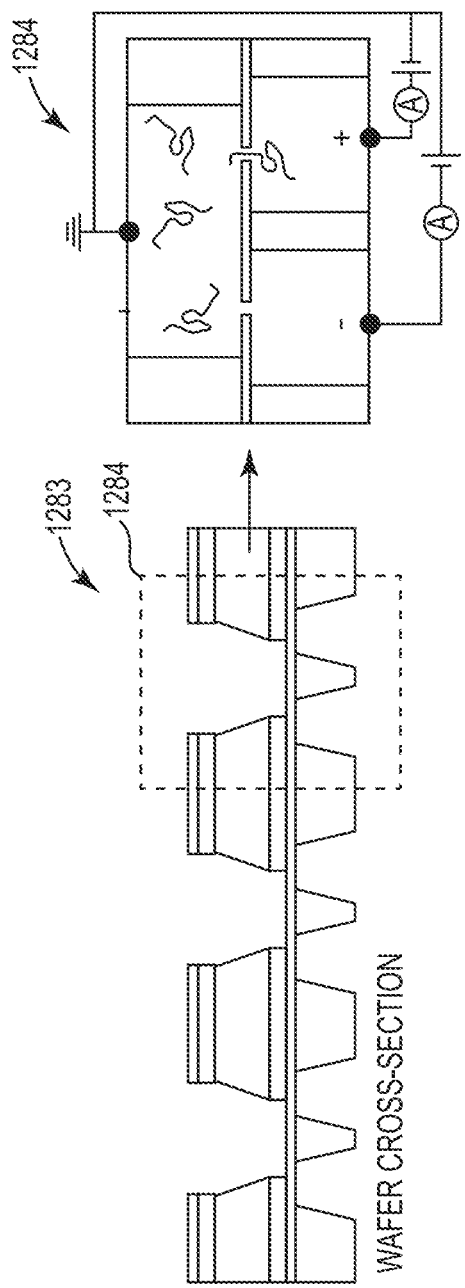
FIGS. 12A-12B illustrates examples of manufacturing an apparatus, in accordance with various embodiments.
Figure 12B:
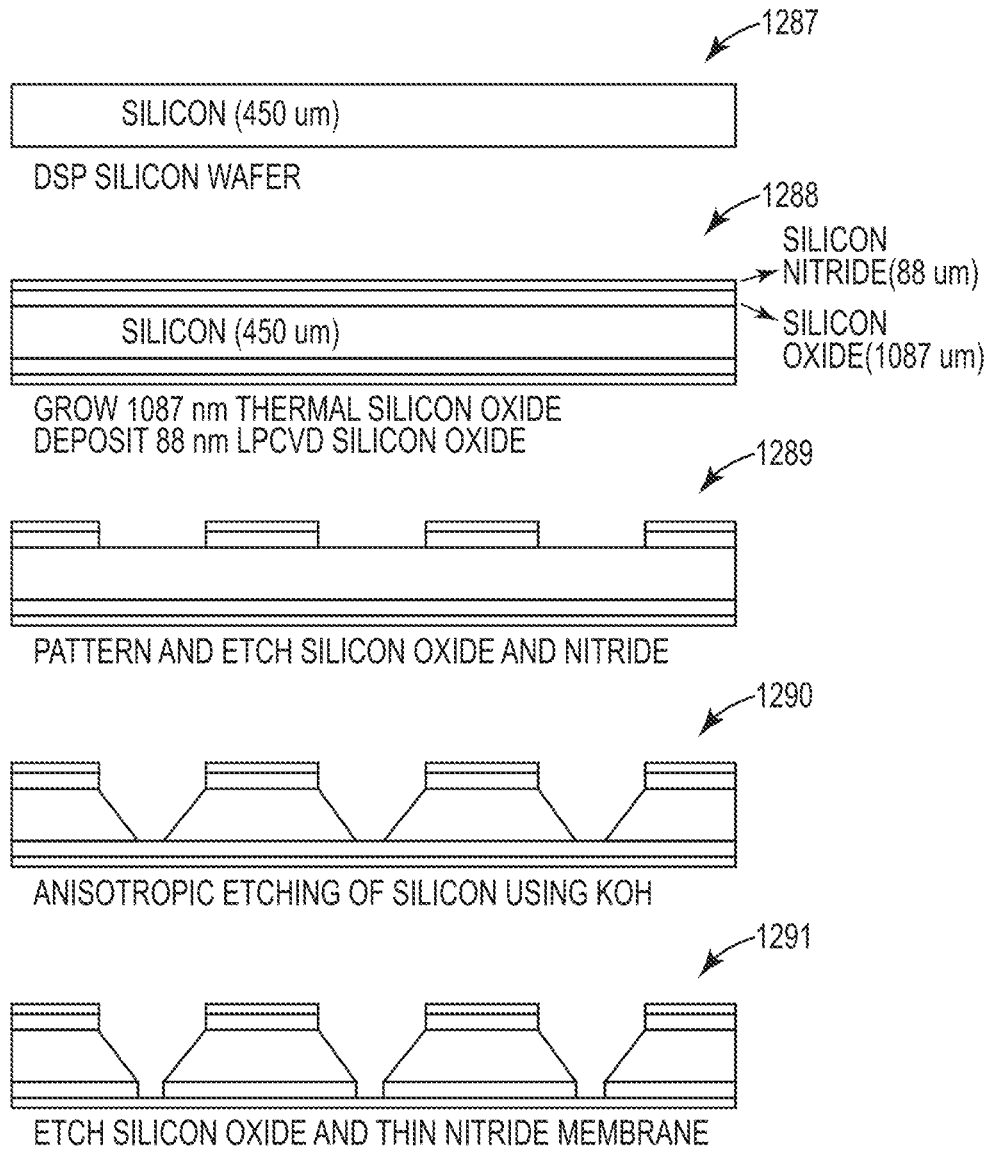

FIGS. 12A-12B illustrates examples of manufacturing an apparatus, in accordance with various embodiments. As previously described, the substrate can include a plurality of chambers. The number of chambers can be on the scale of hundreds, thousands or millions of chambers. Each chamber is designed by repeating the pattern across the substrate, such as across a wafer. A cross-section of the wafer is illustrated by 1283. As further described by FIG. 12B, the wafer includes a plurality of layers of different material (e.g., silicon, silicon nitride, silicon oxide) with different portions of the layers etched to form wells of the chambers that are separated by membranes. The nanopores are formed in the membranes via application of a voltage differential across the membrane, resulting in breakdown of the membrane, as shown by the resulting chamber 1284 (and which is represented by 1284 in the cross-section of the wafer 1283), although embodiments are not so limited. The chambers can be microscale or nanoscale, in various embodiments.

FIG. 12B illustrates a specific example method of forming the plurality of chambers on a substrate, in accordance with various embodiments. The nanopores of the chambers can be fabricated via TEM, FIB, electro-chemical etching and/or electroporation, among other techniques and as previously described. As illustrated, at 1287, a silicon (e.g., 20-600 um thick) wafer is used to form the substrate. At 1288, silicon oxide is grown (e.g., 100-5000 nm) on each side of the silicon wafer and silicon nitride (e.g., 10-500 nm) is deposited on the layer of silicon oxide. At 1289, a layer (e.g., top layer) of the silicon oxide and silicon nitride is patterned and etched. At 1290, the silicon is etched using KOH and at 1291, another layer of the silicon oxide (e.g., bottom layer) is etched to form a thin silicon nitride membrane. In some specific embodiments, the chambers can be in the range of 100 nm-500 um in lateral size (e.g., 100 nm-500 um in depth dimension, 100 nm-500 um in width, and each well being 100 nm-500 um in height, such as 100 nm-500 um for the top well and 20-100 um for the bottom wells), although embodiments in accordance with the present disclosure are not so limited and the above is provided as an example only.

As described above, the nanopores can be formed by electroporation, TEM, and/or other methods. A voltage differential is generated across the membrane in a controlled process to cause breakdown of the silicon nitride membrane and formation of the nanopores. As a specific example, a positive voltage is applied on a first side of the membrane and a negative voltage is applied on a second side of the membrane. In some specific examples, 2-3 nm nanopores can be formed in 2 minutes per nanopore.

A specific example method for manufacturing an apparatus can include forming a plurality of chambers on a substrate, each chamber having at least a first well and two secondary wells separated by dielectric membranes (e.g., such as that illustrated by FIG. 12B). Optionally, the method can include providing a pre-thinned or otherwise weakened areas in the dielectric membranes. The method includes forming flow channels that provide fluidic communication between the plurality of chambers and to flow a sample containing a plurality of proteins to the plurality of chambers. The method further includes feeding solution to the substrate, which may have no nanopores formed, and applying voltage pulses to form the nanopores. For example, the method can include applying an electric potential across each of the dielectric membranes, thereby breaking down a portion of the dielectric membranes and forming a nanopore in each of the plurality of dielectric membranes. A resulting ionic current across the membrane can be measured, which is proportional to the nanopore size. Applying the electric potential across each of the dielectric membranes can include placing the first well at ground and applying a voltage to the two secondary wells to cause a voltage differential there between and across the dielectric membrane. The method further includes providing a feedback signal to determine a size of the nanopore and removing the voltage applied in response thereto.

Nanopores may also be formed on the dielectric membrane, using TEM, FIB, or other methods as previously described. In accordance with various embodiments, the nanopores are formed after the chambers are fabricated but before fluid is introduced. Each nanopore may be positioned on the dielectric membrane according to the coordinates and relative position to other features on the substrate. The nanopore size may be controlled with the electron or ion-beam spot size and formation time.

Figure 13:
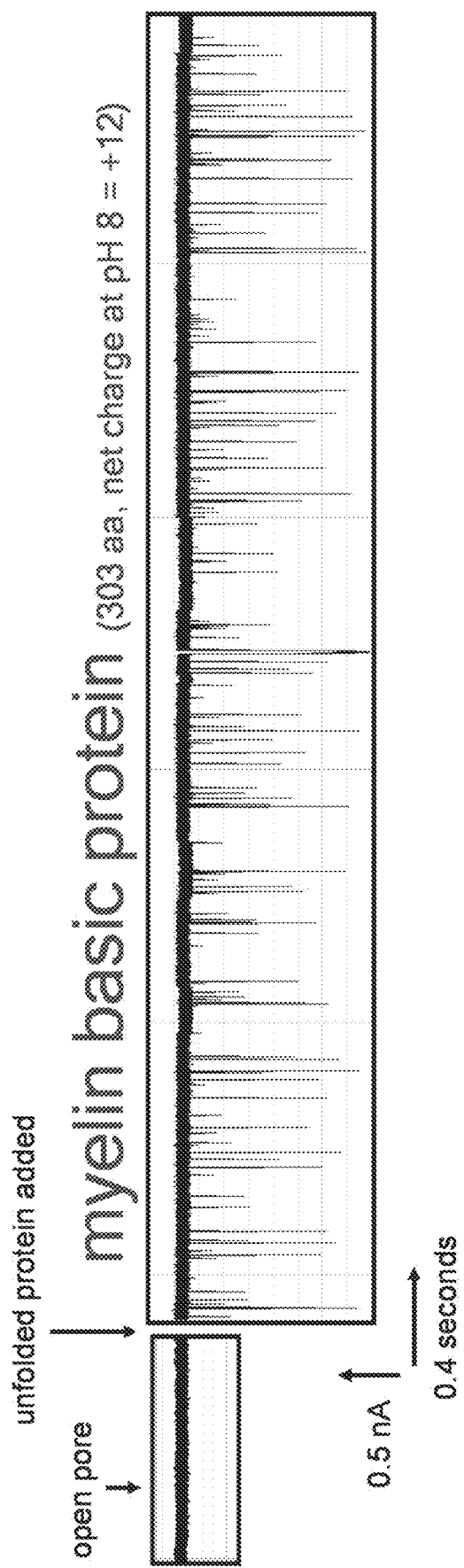
FIG. 13 illustrates an example of detecting events, in accordance with various embodiments.

FIG. 13 illustrates an example of detecting events, in accordance with various embodiments. As previously described, the ionic current through a nanopore is monitored and used to detect translocation events. The nanopore is of a diameter that the single unfolded myelin basic protein can translocate. The ionic current depressions (e.g., dips) are indicative of translocation events.

Figure 14:
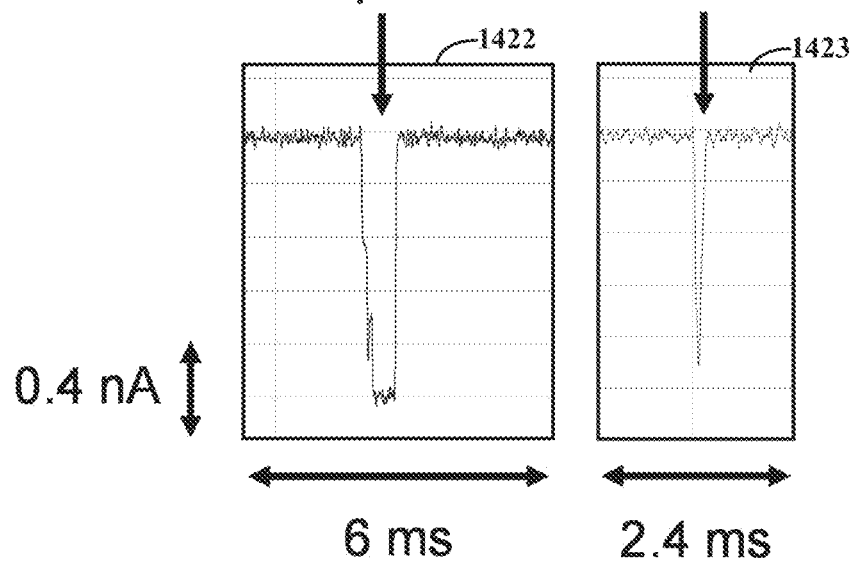
FIG. 14 illustrates an example of detecting events, in accordance with various embodiments.

FIG. 14 illustrates an example of detecting events, in accordance with various embodiments. More specifically, FIG. 14 illustrates two graphs 1422, 1423 showing examples of the myelin basic protein translocating through the nanopore.

Figure 15:
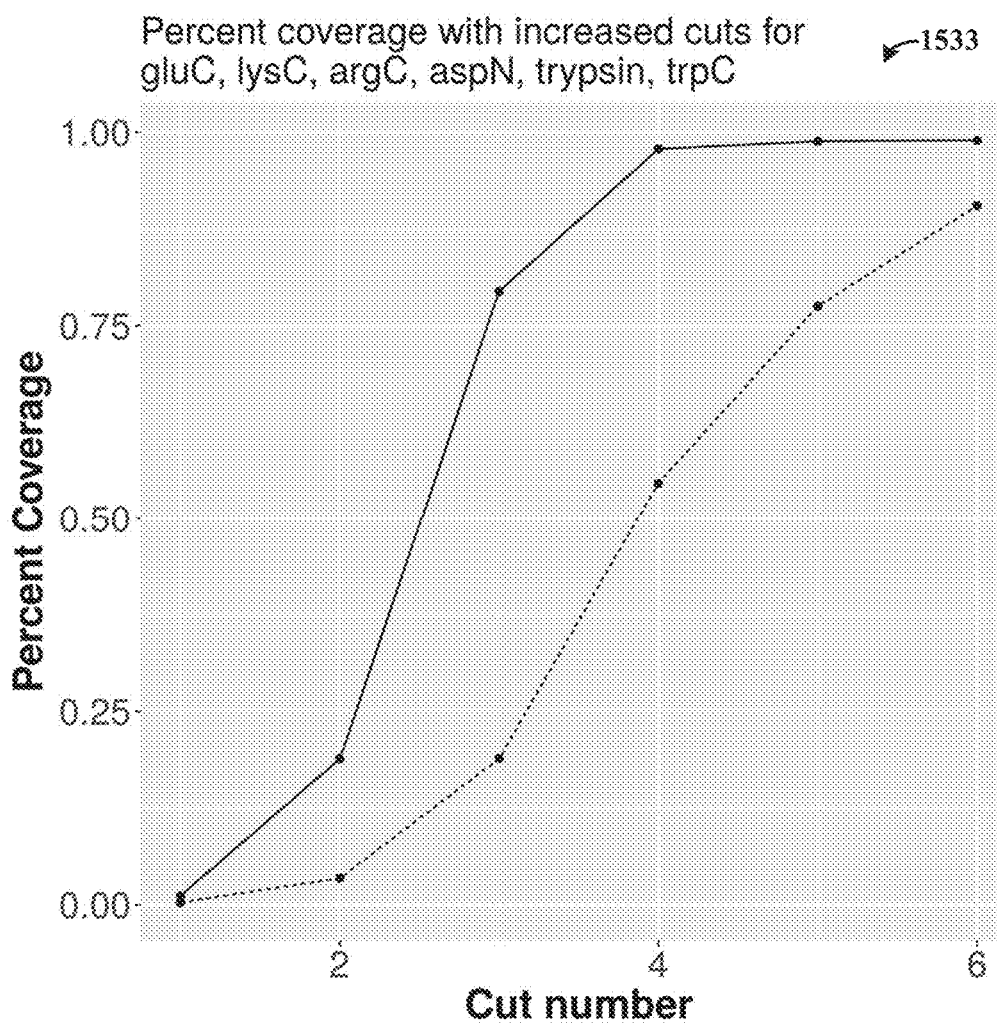
FIG. 15 is a graph illustrating a number of proteases used to identify a protein, in accordance with various embodiments.

FIG. 15 is a graph illustrating a number of proteases used to identify a protein, in accordance with various embodiments. Similarly to FIG. 11F, the graph 1533 illustrates that 97 percent of human proteins can be uniquely identified with exposure to four proteases, although embodiments are not so limited and can include exposure to one to six (or more) proteases. In specific embodiments, the human proteome assessed is from a database, such as Uniprot, and includes around 20,000 protein sequences. An analysis is performed to identify the best sequence of protease cuts that yield unique fingerprint of peptide fragments for the proteome. Parameters include realistic constraints, such as high/low molecular weight cutoff and cutting propensity.

Figure 16A:
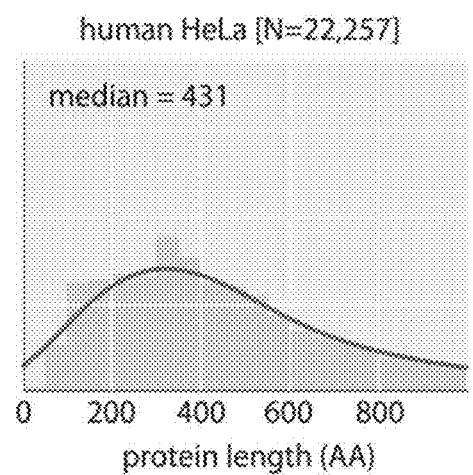
FIGS. 16A-16C illustrate an example bioinformatics model used for identifying proteins, in accordance with various embodiments.
Figure 16B:
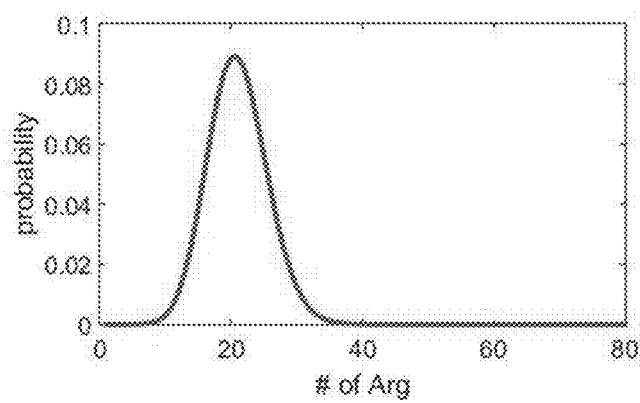
Figure 16C:
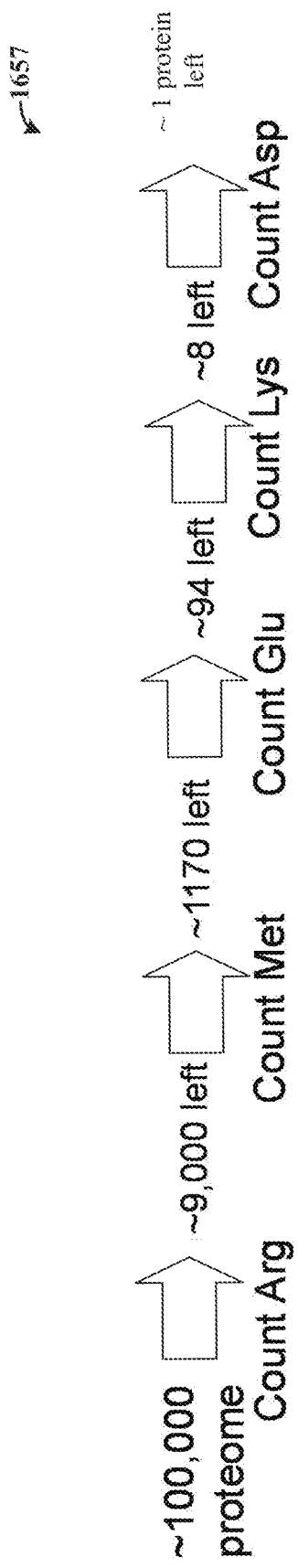

FIGS. 16A-16C illustrate example bioinformatics used for identifying proteins, in accordance with various embodiments. FIG. 16A illustrates an example of the protein length of human proteins, with the average human protein being 400 amino acids in length. As illustrated by FIG. 16B, in a human protein that is 400 amino acids in length, the most likely count of Arginines (Arg) is around 20. FIG. 16C illustrates an example graph 1657 of iteratively narrowing down the identity of a single (e.g., type of) protein from the proteome. Prior to exposing the protein to a protease, the list of potential protein is around 100,000. After exposing to a first protease and counting peptide segments that are indicative of the number of Arg, around 9,000 potential proteins are left. The peptide segments are then exposed to a second protease and peptide segments indicative of the number of Methionine (Met) are counted, and around 1170 potential proteins are left. The process continues until the protein can be identified with some confidence level.

In accordance with various embodiments, a sample is taken and provided to a microfluidic chip that contains a plurality of chambers. The sample can first be pre-processed, as previously described, to purify the proteins. The microfluidic chip, as previously described, is inserted into a microfluidic apparatus having electronic circuitry to drive the proteolysis process. The protein contents are flown across the microfluidic chip having the plurality of chambers used to trap single proteins. As previously described, each of the chambers includes at least a first well and a second well separated from the first well by a membrane with a nanopore. The isolated proteins are cleaved into peptide fragments by introducing one or more sequence-specific proteases. The peptide fragments are counted, in response to each introduction of a protease, by electrophoretically driving the peptide fragments through the nanopore. A traverse of a peptide fragment through a nanopore results in blocking of ionic current and which is used to count translocation events indicative of the number of target cleave sites in the unidentified protein. This is repeated, such as for 1-4 proteases, to uniquely identify a threshold number of proteins in the human proteome. The nanopore chambers can be designed such that each cycle can be performed in a matter of a few minutes (e.g., 1-5 minutes) in an automated fashion. For a purified protein sample or a sample where proteins have been separated by size (for example, by an in-line high-performance liquid chromatography (HPLC) column or two dimensional (2D) separation with isoelectric focusing), identification and quantification can be performed using only a small number of nanopore chambers without single protein dilution.

A number of embodiments involve peptide fragment counting for protein identification after exposing a type of protein to one or more proteases. The translocation signature can depend on the size and length of the translocating peptide fragment, and the frequency of events is proportional to the concentration. By using small nanopores (<4 nm), proteins and peptide fragments can only translocate in an unfolded configuration and one at a time. Counting fragment translocation is a simple, high signal-to-noise measurement that is tolerant to the natural distributions observed in transit time and blocked current depth.

In specific embodiments, the chambers can be split into three chambers, with a positive chamber and a negative chamber separated from a grounded chamber by a membrane having a first nanopore and a second nanopore, such as illustrated by FIG. 2B. The positive and negative chambers can be used to ascertain a net charge in addition to peptide fragment counting, and which can be used to further refine the identification of the protein, such as increasing the speed of identification.

In various embodiments, the bioinformatics model can be updated with feedback from the actual apparatus and/or during manufacturing by an example apparatus. The feedback can include updates in error due to possible fragment loss or other non-idealities.

As used herein, a chamber includes or refers to two or more wells used to perform an evaluation experiment on a protein. The apparatus, which can include a plurality of wells, can have wells that are in fluidic communication via fluidic channels used to flow the sample therein. A well includes or refers to a reservoir for fluid collection. The wells of a chamber can be separated from one another, and at least two of the wells are in fluidic communication with one another via a nanopore. The wells can be formed by patterning and etching of a plurality of layers of material of the substrate, in various embodiments. A nanopore includes or refers to a channel (e.g., a hole) formed in the membrane that separates two wells and which has a diameter on an order of nanometers, such as 1-4 nm. A microfluidic chip includes or refers to a set of fluidic channels etched or molded into a material, such as a substrate formed of different layers of material. The microfluidic chip can be used to input a sample of fluid and to perform an evaluation experiment (e.g., a test) thereon. The fluid can be on the order of nanoliters or femtoliters. A microfluidic system includes or refers to a set of devices, including a microfluidic chip and circuitry, used to perform a test on a sample of fluids. A protein includes or refers to a biomolecule consisting of one or more chains of amino acids. As may be appreciated, a complete protein is usually folded into a three-dimensional structure. The three-dimensional structure can be formed by the primary structure (e.g., the amino acid sequence), the secondary structure (e.g., repeating local structures stabilized by hydrogen bonds, such as a-helixes, B-sheets, and turns), the tertiary structure (e.g., shape of a single protein molecule which includes the spatial relationship of secondary structures to one another and which are stabilized by nonlocal interactions) and the quaternary structure (e.g., formed from several protein molecules that function as a single protein complex). A peptide fragment includes or refers to a chain of amino acids that is a subset of the protein. The peptide fragments are generated by digestion of the protein via a protease. A single protein includes or refers to a single type of protein—where there are many copies of that type of protein and the copies are isolated in a single or multiple chambers but not at the single molecule level- or a single unique protein (e.g., at the single molecule level). As may be appreciated, any recitation of "single protein" as provided herein, in accordance with various embodiments, can be referring to a single type (or class) of protein, although embodiments are not so limited. A denatured protein includes or refers to the primary structure of the protein, e.g., the secondary and tertiary (and optional quaternary) structure are disrupted and the primary structure remains the same. A denaturant includes or refers to the stress and/or compound that causes denaturing of proteins, including loss of secondary and tertiary (and optional quaternary) structures present in their native state. The denaturant can include a strong acid or base, a concentrated inorganic salt, an organic solvent, radiation and/or heat. A protease includes or refers to an enzyme that breaks down proteins and peptides into peptide fragments. Target cleavage sites includes or refers to a site at which a protease split peptide bonds, such as at or between two amino acid pairs. Translocation includes or refers to a change of location of a molecules through a nanopore. A bioinformatics model includes or refers to computer-readable instructions stored on memory that includes identification of potential proteins and cleavage rules, that when executed by a respective target processing circuitry is used to evaluate at least one protein in the sample. For example, when executed, the bioinformatics model is used to identify whether or not a particular protein is present in the sample, quantify the particular protein or multiple proteins, and/or an iteratively narrowing down identification of one or more proteins in the sample. In specific embodiments, the bioinformatics model includes a lookup table that can be searched (e.g., manually and/or by processing circuitry). Cleavage rules include or refer to identification of target cleavage sites of the protease (e.g., split peptide bonds at the target cleavage sites) and non-idealities (e.g., fragments too small, protease efficiencies, secondary cleavage sites) of the protease. In a number of embodiments, software programming can be used to automatically predict the cleavage rules, including such cleavage sites that are both the target and secondary cleavage sites.

The skilled artisan would recognize that various terminology as used in the Specification (including claims) connote a plain meaning in the art unless otherwise indicated. As examples, the Specification describes and/or illustrates aspects useful for implementing the claimed disclosure by way of various circuits or circuitry which may be illustrated as or using terms such as blocks, modules, device, system, unit, controller, and/or other circuit-type depictions (e.g., reference numerals 104, 106, 108 of FIG. 1A depict a block/module as described herein). Such circuits or circuitry are used together with other elements to exemplify how certain embodiments may be carried out in the form or structures, steps, functions, operations, activities, etc. For example, in certain of the above-discussed embodiments, one or more modules are discrete logic circuits or programmable logic circuits configured and arranged for implementing these operations/activities, as may be carried out in the approaches shown in FIG. 1 and FIG. 6. In certain embodiments, such a programmable circuit is one or more computer circuits, including memory circuitry for storing and accessing a program to be executed as a set (or sets) of instructions (and/or to be used as configuration data to define how the programmable circuit is to perform), and an algorithm or process as described at FIGS. 5A-5B is used by the programmable circuit to perform the related steps, functions, operations, activities, etc. Depending on the application, the instructions (and/or configuration data) can be configured for implementation in logic circuitry, with the instructions (whether characterized in the form of object code, firmware or software) stored in and accessible from a memory (circuit).

Various embodiments described above, may be implemented together and/or in other manners. One or more of the items depicted in the present disclosure can also be implemented separately or in a more integrated manner, or removed and/or rendered as inoperable in certain cases, as is useful in accordance with particular applications. In view of the description herein, those skilled in the art will recognize that many changes may be made thereto without departing from the spirit and scope of the present disclosure.

What is claimed is:

1. A method comprising:
    isolating a single protein from a sample in a chamber having at least a first well and a second well separated from the first well by a membrane with a nanopore, the nanopore providing fluidic communication between the first and second wells;
    cleaving the single protein into a plurality of peptide fragments via exposure to a protease in the first well;
    translocating the plurality of peptide fragments through the nanopore by applying an electric potential after cleavage of the single protein by the protease;
    detecting events indicative of the translocations of the plurality of peptide fragments cut from the single protein through the nanopore and to the second well; and
    measuring a duration of the detected events and using the measured duration to provide an estimate of the length of the plurality of peptide fragments or to detect clogging of the nanopore and unclogging the nanopore by reversing a bias across the nanopore.

2. The method of claim 1, wherein the electric potential imparts an electrophoretic force that is generated by applying the electric potential across the nanopore, and the detected events include changes in ionic current through the nanopore, the method further including determining an estimated number of target cleavage sites within the single protein based on the detected events, wherein the protease is configured and arranged to cleave proteins by splitting peptide bonds at the target cleavage sites in the single protein or peptide fragment.

3. The method of claim 2, wherein determining the estimated number of the target cleavage sites is based on cleavage rules specific to each protease including identification of the protease configured and arranged to split peptide bonds at the target cleavage sites in the single protein or peptide fragment and efficiency and specificity of the protease, the method further including correlating the number of translocations with the estimated number of the target cleavage sites to narrow down an identity of the single protein by iteratively introducing additional proteases to the first well of the chamber, to additional wells of the chamber, or to an additional chamber in fluidic communication with the chamber.

4. The method of claim 1, further including isolating a plurality of single denatured proteins from the sample in a plurality of chambers, wherein each of the plurality of chambers has at least the first well and the second well separated from the first well by a membrane with a nanopore and a third well separated from the first well by a membrane with another nanopore, and detecting events after cleaving each of the plurality of single denatured proteins in each respective chamber via exposure to the protease.

5. The method of claim 1, further including:
    sequentially exposing the single protein to each of a plurality of different proteases, and determining numbers of peptide fragments derived from the exposure to each of the plurality of different proteases; and
    identifying the single protein, with a confidence value, based on estimated numbers of target cleavage sites in the single protein determined using the detected events and a bioinformatics model, the bioinformatics model including:
        identification of a plurality of potential proteins with identified target cleavage sites,
        cleavage rules that each of the plurality of different proteases are subject to including protease efficiencies, non-primary cleavage sites, and non-specific cleavage sites, and
        non-idealities including identification of peptide fragments that do not generate a change in ionic current.

6. The method of claim 1, wherein isolating the single protein from the sample further includes:
    flowing a solution through the chamber,
    while flowing the solution, creating a voltage differential between the first well, the second well, and a third well;
    detecting a change in ionic current through the nanopore, which is indicative of the single protein translocating from the first well to one of the second well and the third well; and
    in response to the detection, removing the voltage differential.

7. The method of claim 1, wherein the single protein is denatured and the method further includes closing fluidic access to the chamber from a remainder of the sample to isolate the single protein.

8. The method of claim 1, wherein the chamber includes the second well and a third well each separated from the first well by the membrane and another membrane and each directly in fluidic communication with the first well by respective nanopores, the method further including, after cleaving the single protein:
    applying a first polarity voltage to the second well and applying a second polarity voltage to the third well, wherein the first well is grounded;
    detecting changes in ionic current through the nanopores, which are indicative of translocations of the plurality of peptide fragments cleaved from the single protein to the second and/or third wells; and determining the number of positively and negatively charged peptide fragments of the single protein based on the number of detected changes in the ionic current through each respective nanopore.

9. The method of claim 1, further including repeating detecting of the events which are indicative of the number of peptide fragments cleaved from the single protein responsive to exposure to the protease by reversing a bias across the nanopore and repeating the translocation of the peptide fragments through the nanopore from the second well to the first well and detecting further events in response thereto.

10. The method of claim 1, further including forming the nanopore in the membrane, wherein the nanopore is of a size to allow translocation of the single protein, without allowing simultaneous passing of a second protein or while allowing simultaneous passing of a second single protein at below a threshold frequency.

11. The method of claim 1, further including detecting clogging of the nanopore, responsive to a change in an ionic current through the nanopore for greater than a threshold period of time, and unclogging the nanopore by applying the reverse bias to the nanopore.

12. An apparatus, comprising:
flow channels configured and arranged to flow a sample containing a plurality of proteins there through;
a plurality of chambers in fluidic communication with the flow channels, wherein each of the plurality of chambers includes at least a first well and two secondary wells separated from the first well by membranes having a nanopore that is configured and arranged to provide fluidic communication between the at least first well and the two secondary wells;
fluidic access circuitry configured and arranged to selectively provide fluidic access to the plurality of chambers and selectively provide different proteases to respective chambers to cleave single proteins of the plurality of proteins into a plurality of peptide fragments; and
electrical circuitry configured and arranged to drive translocations of the single proteins and the plurality of peptide fragments across the nanopores, and to output electrical signals indicative of the translocations; and
processing circuitry configured and arranged to:
detect events indicative of the translocations of the plurality of peptide fragments through the nanopores and into at least one of the two secondary wells based on the output electrical signals; and
cause the electrical circuitry to reverse a bias across the nanopores and repeat the translocation of the plurality of peptide fragments through the nanopores and detect further events in response thereto.

13. The apparatus of claim 12, wherein the different proteases are attached to beads to mitigate translocation and/or denaturation.

14. The apparatus of claim 12, wherein the fluidic access circuitry includes a dielectric layer configured and arranged to move between an open-fluid-access state and a closed state that blocks fluidic access to the plurality of chambers.

15. The apparatus of claim 12, further including a module, wherein the sample is pre-processed through the module that performs at least one of:
exposing the sample to protease inhibitors configured and arranged to prevent premature proteolysis;
fractionation by protein characteristics; and
filtering to remove sample components larger in diameter than a denatured protein.

16. The apparatus of claim 12, wherein the electrical circuitry includes sets of electrodes respectively coupled to the first well and the two secondary wells of each of the plurality of chambers and the output electrical signals are determined from measures of each of the sets of electrodes on each side of the respective membranes, wherein the sets of electrodes are configured and arranged to apply a bias across the nanopores.

17. The apparatus of claim 12, wherein the electrical circuitry is configured and arranged to apply first and second voltage differentials between the first well and each of the two secondary wells of each of the plurality of chambers and measure the electrical signals indicative of ionic current flowing through the nanopores, wherein a change in the ionic current is indicative of the translocations.

18. The apparatus of claim 12, the apparatus further including processing circuitry configured and arranged to, responsive to the output electrical signals indicative of the translocations:
detect translocations of the single proteins of the plurality of proteins, and communicate the detection to the fluidic access circuitry for isolating the single proteins;
adjust translocation voltages based on one or more of a number, a duration, and timing of translocation events;
detect the events indicative of the translocation of the peptide fragments, which are cleaved from the single proteins by the proteases, through the nanopores responsive to exposure of the single proteins to at least one of the different proteases;
optionally, process signals indicative of the detected events into a measure of translocation counts that are stored on-chip, and interrogated and reset periodically by the processing circuitry; and
determine a number of peptide fragments generated from the single proteins as cleaved by exposure to the different proteases based on the number of detected events.

19. The apparatus of claim 18, wherein the processing circuitry is further configured and arranged to combine information identified from the detected events from the plurality of chambers across a single chip to produce concentration information for proteins present in the sample.

20. The apparatus of claim 18, wherein the processing circuitry is further configured and arranged to measure a duration of the detected events and use the measured duration to provide an estimate of the length of the translocated peptide fragments or to detect clogging of the nanopore and cause the electrical circuitry to reverse a bias across the nanopore to unclog the nanopore.

* * * * *